United States Patent
Fisker et al.

(10) Patent No.: US 11,478,330 B2
(45) Date of Patent: *Oct. 25, 2022

(54) DENTAL PREPARATION GUIDE

(71) Applicant: 3SHAPE A/S, Copenhagen K (DK)

(72) Inventors: Rune Fisker, Virum (DK); Nikolaj Deichmann, Klagshamn (SE)

(73) Assignee: 3SHAPE A/S, Copenhagen K (DK)

( * ) Notice: Subject to any disclaimer, the term of this patent is extended or adjusted under 35 U.S.C. 154(b) by 132 days.

This patent is subject to a terminal disclaimer.

(21) Appl. No.: 17/126,382

(22) Filed: Dec. 18, 2020

(65) Prior Publication Data

US 2021/0169607 A1 Jun. 10, 2021

Related U.S. Application Data

(63) Continuation of application No. 16/208,719, filed on Dec. 4, 2018, now Pat. No. 10,918,458, which is a
(Continued)

(30) Foreign Application Priority Data

Nov. 28, 2011 (DK) .......................... PA 2011 00925

(51) Int. Cl.
*A61C 1/08* (2006.01)
*G16B 5/00* (2019.01)
(Continued)

(52) U.S. Cl.
CPC ............ *A61C 1/082* (2013.01); *A61C 9/0053* (2013.01); *A61C 13/0004* (2013.01);
(Continued)

(58) Field of Classification Search
CPC ... A61C 1/082; A61C 9/0053; A61C 13/0004; B29C 64/386; G06F 30/00; G16B 5/00
See application file for complete search history.

(56) References Cited

U.S. PATENT DOCUMENTS

| 6,767,575 B1 | 7/2004 | Huss et al. |
| 7,393,211 B2 | 7/2008 | Wilkinson |

(Continued)

FOREIGN PATENT DOCUMENTS

| CN | 1410032 A | 4/2003 |
| CN | 101547661 A | 9/2009 |

(Continued)

OTHER PUBLICATIONS

Hoppe et al., "Surface Reconstruction from Unorganized Points", Computer Graphics, Jul. 1992, pp. 71-78, vol. 26, No. 2.
(Continued)

*Primary Examiner* — Ziaul Karim
(74) *Attorney, Agent, or Firm* — Buchanan Ingersoll & Rooney PC

(57) ABSTRACT

A method for validating a preparation of at least one tooth in a prepared set of teeth for determining whether the prepared tooth is capable of accepting a dental restoration includes obtaining a virtual dental preparation guide configured for validating the preparation of the at least one tooth; obtaining a digital 3D representation of the prepared set of teeth; visualizing the virtual dental preparation guide together with the digital 3D representation of the prepared set of teeth; and validating from the visualization of the virtual dental preparation guide together with the digital 3D representation of the prepared set of teeth whether the prepared at least one tooth is shaped such that it can accept the dental restoration.

22 Claims, 17 Drawing Sheets

Related U.S. Application Data continuation of application No. 14/361,217, filed as application No. PCT/EP2012/073605 on Nov. 26, 2012, now Pat. No. 10,251,726.

(60) Provisional application No. 61/564,191, filed on Nov. 28, 2011.

(51) Int. Cl.
   *B29C 64/386* (2017.01)
   *G06F 30/00* (2020.01)
   *A61C 13/00* (2006.01)
   *A61C 9/00* (2006.01)

(52) U.S. Cl.
   CPC ............ *B29C 64/386* (2017.08); *G06F 30/00* (2020.01); *G16B 5/00* (2019.02)

(56) References Cited

U.S. PATENT DOCUMENTS

| | | | |
|---|---|---|---|
| 8,651,858 B2 | 2/2014 | Berckmans et al. | |
| 2002/0110786 A1 | 8/2002 | Dillier | |
| 2002/0180760 A1 | 12/2002 | Rubbert et al. | |
| 2003/0215764 A1 | 11/2003 | Kopelman et al. | |
| 2005/0250075 A1* | 11/2005 | Taub | G06T 17/00 433/213 |
| 2007/0015111 A1 | 1/2007 | Kopelman et al. | |
| 2008/0261165 A1* | 10/2008 | Steingart | B33Y 50/00 433/24 |
| 2009/0191503 A1 | 7/2009 | Matov et al. | |
| 2009/0298017 A1* | 12/2009 | Boerjes | A61B 5/4547 433/214 |
| 2011/0066267 A1 | 3/2011 | Schmitt | |
| 2011/0159451 A1 | 6/2011 | Kuo et al. | |
| 2012/0015316 A1 | 1/2012 | Sachdeva et al. | |
| 2012/0143364 A1 | 6/2012 | Mcleod et al. | |
| 2012/0282567 A1 | 11/2012 | Nilsson | |
| 2013/0041630 A1 | 2/2013 | Gilles et al. | |
| 2013/0060532 A1 | 3/2013 | Clausen et al. | |
| 2013/0226534 A1 | 8/2013 | Fisker et al. | |
| 2013/0316302 A1 | 11/2013 | Fisker | |

FOREIGN PATENT DOCUMENTS

| | | |
|---|---|---|
| CN | 101784238 A | 7/2010 |
| CN | 101878005 A | 11/2010 |
| DE | 4012327 A1 | 10/1991 |
| DE | 102010010069 A1 | 9/2011 |
| EP | 0250623 A1 | 1/1988 |
| JP | 2002272763 A | 9/2002 |
| JP | 2011500142 A | 1/2011 |
| KR | 20110116197 A | 10/2011 |
| WO | 9426200 A1 | 11/1994 |
| WO | 0245522 A1 | 6/2002 |
| WO | 2006089165 A2 | 8/2006 |
| WO | 2008043056 A2 | 4/2008 |
| WO | 2008063115 A1 | 5/2008 |
| WO | 2009048475 A1 | 4/2009 |
| WO | 2009070470 A1 | 6/2009 |
| WO | 2010086459 A1 | 8/2010 |
| WO | 2010105628 A2 | 9/2010 |
| WO | 2011103879 A1 | 9/2011 |
| WO | 2012076574 A2 | 6/2012 |

OTHER PUBLICATIONS

Office Action dated Jul. 12, 2012, by the Danish Patent Office in corresponding Danish Patent Application No. 25553489. (4 pages).

First Office Action issued in corresponding Chinese Patent Application No. 201710796862.3, dated Oct. 8, 2019, with English Translation, (13 pages).

Office Action (Notice of Reasons for Rejection) dated Jul. 11, 2017, by the Japanese Patent Office in corresponding Japanese Patent Application No. 2014-543850. (4 pages).

Office Action dated Jul. 12, 2012, by the Danish Patent Office in corresponding Danish Patent Application No. DA 2011 00925. (Previously filed with fee on May 14, 2020 which listed the CVR-/P number instead of the Danish Application number.).

International Search Report (PCT/ISA/210) dated Aug. 14, 2013, by the European Patent Office as the International Searching Authority for International Application No. PCT/EP2012/073605.

Written Opinion (PCT/ISA/237) dated Aug. 14, 2013, by the European Patent Office as the International Searching Authority for International Application No. PCT/EP2012/073605.

\* cited by examiner

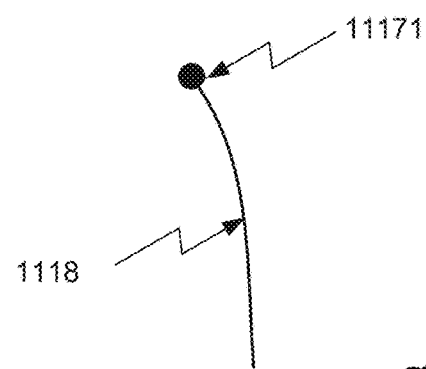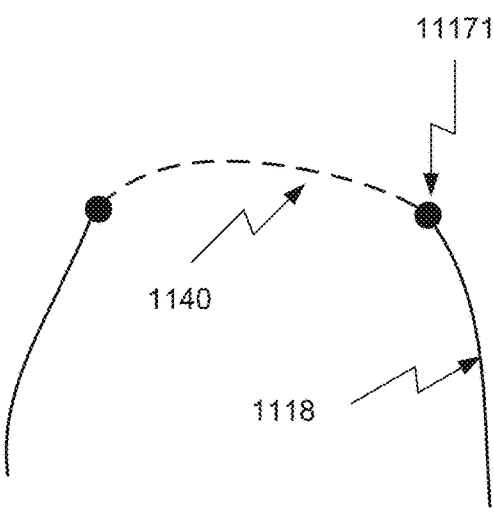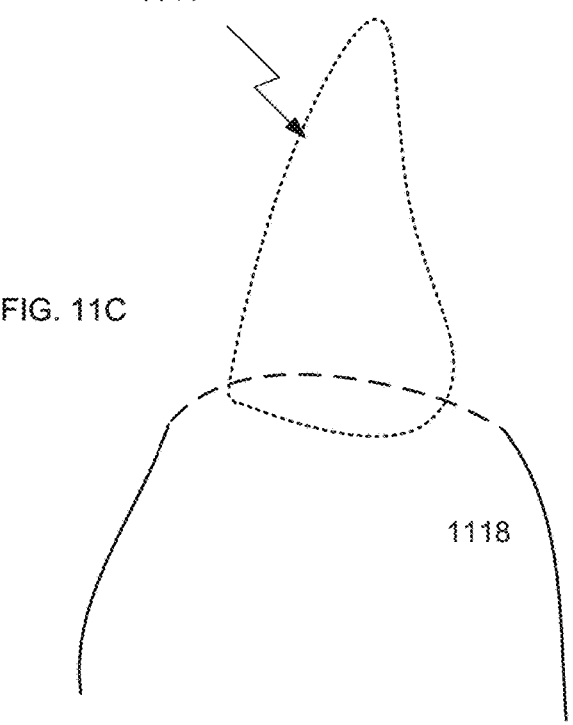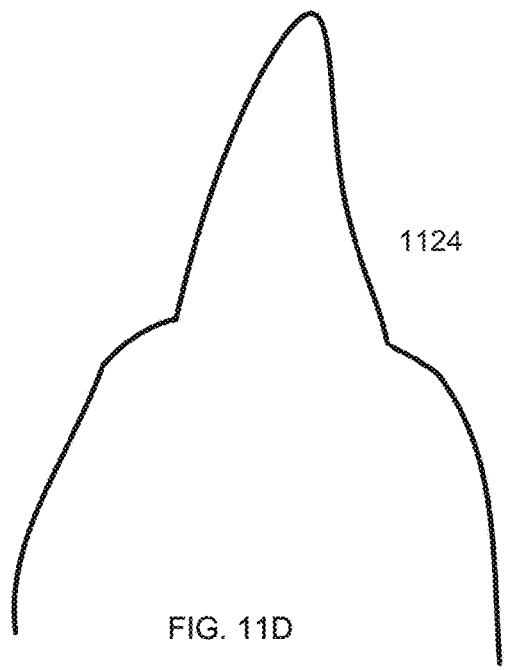

DENTAL PREPARATION GUIDE

The present application is a continuation of U.S. patent application Ser. No. 16/208,719, filed on Dec. 4, 2018, which is a continuation of U.S. Ser. No. 14/361,217, filed on May 24, 2014, and which is a national stage application of PCT/EP2012/073605, which was filed on Nov. 26, 2012, and which claims the benefit of U.S. Ser. No. 61/564,191, which was filed on Nov. 28, 2011, and which claims the priority of Danish Patent Application No. PA 2011 00925, which was filed on Nov. 28, 2011. The subject matter of U.S. patent application Ser. No. 16/208,719, U.S. Ser. No. 14/361,217; PCT/EP2012/073605; U.S. Ser. No. 61/564, 191; and Danish Patent Application No. PA 2011 00925 is incorporated herein by reference.

This invention generally relates a dental preparation guide configured for validating the preparation of at least one tooth for a dental restoration. More particularly, the invention relates to a method for generating the dental preparation guide, a method for using such a dental preparation guide and a user interface and a system for designing and using such a dental preparation guide.

When a patient's tooth is ill or dead, it is often recommended that a part of the tooth is removed and replaced by a dental restoration, such as a crown restoration, which can restore the mechanical strength and the aesthetic appearance of the tooth. In other cases, the tooth is too ill or is broken such that it cannot support a restoration and it has to be extracted completely. In such cases the dental restoration can be a bridge restoration with a pontic which is designed to replace the ill or broken tooth and two crowns surrounding the pontic. The neighboring teeth are then prepared for the crowns of the bridge restoration.

Both while preparing a single tooth for a crown restoration and while preparing neighboring teeth for the crowns of a bridge, the dentist grinds away some tooth material to form a prepared tooth or teeth which can accept the dental restoration. The material which is removed makes space for the dental restoration such that the when the dental restoration is arranged in the patient's mouth, the restored tooth or teeth can have the same or a similar shape or size as prior to the preparation.

The desired shape of the dental restoration is sometimes known when the dentist starts preparing the teeth and this knowledge can be used to create a dental preparation guide which the dentist can use for guiding the preparation of the tooth.

In some prior art methods for the manufacture of dental preparation guides, the validation surface is defined from a physical teeth model, such as a Gypsum model grinded to what could be a good preparation shape and size and which is believed to allow space for the dental restoration to be inserted at the prepared tooth. Inaccuracy in the production of this physical teeth model will result in an accuracy in the shape of the dental preparation guide and hence in the shape of the prepared tooth.

In the prior art method disclosed in US2011/0159451 the dental preparation guide is generated by superimposing a virtual model of the tooth prior to the preparation with a virtual model expressing a target shape of the restored tooth. This approach also has some disadvantages as described below.

The present invention solves the problems of the prior art methods. Disclosed is a method for generating a dental preparation guide configured for validating the preparation of at least one tooth for a dental restoration, said method comprising:

a: obtaining a digital 3D representation of a pre-prepared set of teeth;

b: virtually removing the at least one tooth from the digital 3D representation of the pre-prepared set of teeth, such that a digital 3D representation of a remaining set of teeth is formed;

c: providing a virtual target dental restoration expressing a target shape of the dental restoration;

d: creating a virtual validation surface for the dental preparation guide based on the virtual target dental restoration, where the validation surface is such that the preparation of the at least one tooth can be validated by the dental preparation guide; and e: creating a virtual preparation guide surface by combining the virtual validation surface and at least part of the surface of the digital 3D representation of the remaining set of teeth.

Disclosed is a method for validating a preparation of at least one tooth in a prepared set of teeth for determining whether the prepared tooth is capable of accepting a dental restoration, said method comprising:

obtaining a virtual dental preparation guide configured for validating the preparation of the at least one tooth;

obtaining a digital 3D representation of the prepared set of teeth;

visualizing the virtual dental preparation guide together with the digital 3D representation of the prepared set of teeth; and validating from the visualization of the virtual dental preparation guide together with the digital 3D representation of the prepared set of teeth whether the prepared at least one tooth is shaped such that it can accept the dental restoration.

In some embodiments, the obtained virtual dental preparation guide is created using an embodiment of the method for generating a dental preparation guide.

The disclosed methods where a validation surface of a dental preparation guide for validating the preparation of a tooth is created at least in part using digital 3D representations of the patient's set of teeth solves the inaccuracy problem arising when defining the validation surface solely from a physical teeth model.

The dental preparation guide can be a virtual guide or a physical guide, where the validation surface in both cases is such that the tooth preparation can be validated.

In the virtual case, the dental preparation guide is a virtual unit which can be arranged in relation to a digital 3D representation of the patient's set of teeth In the physical case, the physical dental preparation guide is manufactured from the created virtual preparation guide and can be arranged in the patient's mouth and physical contact or distance between surfaces can be used for the validation.

The physical dental preparation guide can be manufactured based on the virtual dental preparation guide, such that the physical dental preparation guide comprises a validation surface corresponding to the virtual validation surface. In some cases the physical dental preparation guide is such that when it is arranged in relation to the set of teeth in the patient's mouth, the validation surface defines a boundary inside which the prepared tooth must be confined.

By generating the dental preparation guide from virtual surfaces created from digital 3D representations of the patient's set of teeth, or using the virtual surfaces themselves as part of a virtual dental preparation guide, the present invention solves the inaccuracy problem that can be experienced when working with physical models of the set of teeth.

For a virtual dental preparation guide, the validation of the tooth preparation can be based on a visualization of the dental preparation guide together with a digital 3D representation of the patient's set of teeth, e.g. when at least some preparation of the tooth has been carried out and the dentist wishes to validate the preparation to see whether further preparation is required.

For some embodiments of a physical dental preparation guide according to the present invention, the validation of the tooth preparation is based on a registration of the physical contact between the dental preparation guide and the prepared tooth or teeth. After some preparation of the tooth, the dentist may wish to validate the preparation of a tooth to see whether further preparation is required. He then places the dental preparation guide at the patient's teeth and evaluates if the preparation is complete or further removal of teeth material is required. In some cases, the dental preparation guide is designed to provide that is does not collide with the prepared tooth when the preparation is complete.

In some embodiments, the digital 3D representation of the remaining set of teeth comprises a section of the patient's gingiva. The virtual preparation guide surface can then include at least a part of the gingiva and a manufactured dental preparation guide will be able to engage this section of the gingiva when the dental preparation guide is used in the patient's mouth. The gingiva hence provides support for the dental preparation guide which can be arranged correctly relative to the prepared tooth even when the entire tooth surface is modified.

In some embodiments, the digital 3D representation of the remaining set of teeth comprises part of at least one of the neighboring teeth. This may be the closest neighbor tooth or teeth, and/or teeth further away from the prepared tooth. The virtual preparation guide surface can then include at least a part of the surface of the neighboring teeth and a manufactured dental preparation guide will be able to engage these teeth when the dental preparation guide is used in the patient's mouth. The neighbor teeth hence provides support for the dental preparation guide which can be arranged correctly relative to the prepared tooth even when the entire tooth surface is modified. The part of the dental preparation guide which contacts the neighbor teeth may be formed as wings surrounding the part of the dental preparation guide which faces the prepared tooth.

Prior art methods, such as the method described in US2011/0159451, where the dental preparation guide is designed only from the surface of the tooth which is to be prepared are inadequate in cases where the entire surface of the tooth is to be modified by the preparation of the tooth. In such cases, e.g. when the dental restoration is a full crown, the prior art dental preparation guide has no surface which can support the dental preparation guide to ensure that it is properly aligned to the prepared tooth. Embodiments of the present invention, where the digital 3D representation of the remaining set of teeth comprises one or more neighboring teeth and/or the gingiva solves this problem since the dental preparation guide then has a surface which shaped to engage a portion of the patient's set of teeth which is not modified during the preparation. The dental preparation guide is still directed towards its correct arrangement relative to the prepared tooth even when the whole surface of the tooth is modified during the preparation.

Preferably, the virtual dental preparation guide is shaped such that the dental restoration can be realized and can be accepted by the prepared tooth when this is prepared according to the virtual dental preparation guide.

In some embodiments, the method for validating a preparation using the dental preparation guide comprises visualizing the virtual preparation guide surface or the virtual validation surface together with the digital 3D representation of the remaining set of teeth. This may e.g. be the case when the virtual dental preparation guide is formed only by the virtual preparation guide surface or the virtual validation surface. When using a virtual dental preparation guide to validate the preparation, there is no need to e.g. shell the virtual preparation guide surface to provide a solid model which can be manufactured using direct digital manufacturing. It may hence be advantageous that the virtual dental preparation guide only has one surface, such as the virtual preparation guide surface or the virtual validation surface.

Disclosed is a method for manufacturing a dental preparation guide configured for validating a preparation of at least one tooth in a set of teeth for a dental restoration, said method comprising:

generating a virtual dental preparation guide using the method according to any of the embodiments; and
manufacturing the dental preparation guide from said virtual dental preparation guide using direct digital manufacturing.

When arranged in the patient's mouth in relation to the patient's teeth, the manufactured dental validation tool can validate the tooth preparation such that the dentist can decide whether the preparation is complete or more preparation work is required.

Disclosed is a dental preparation guide configured for validating a preparation of at least one tooth in a set of teeth for a dental restoration, said dental preparation guide comprising a tooth facing surface shaped according to the virtual validation surface generated by using the method according to one of the embodiments.

In some embodiments, the dental preparation guide is configured for validating the tooth preparation with respect to a target tooth preparation, where the target tooth preparation may be defined prior to any preparation of the tooth. This may be the case when the dentist or a dental technician has designed the dental restoration prior to the preparation of the tooth and has created a target tooth preparation based on the designed dental restoration. This approach has the advantage that the dentist immediately when starting preparing the tooth can obtain guidance on how the tooth preferably shall be prepared. In difficult cases such as when preparing a number of rotated teeth for a bridge restoration, this may be highly advantageous. The target tooth preparation may also be defined during the procedure such as after an initial preparation step. This approach has an advantage when the tooth which is to be prepared is ill and detailed knowledge of the robustness of the inner portions of the tooth is unknown.

In some embodiments, the generated dental preparation guide is such that it can be arranged relative to the patient's set of teeth with the validation surface facing the tooth. The tooth may be that of the pre-prepared set of teeth or that of the prepared set of teeth.

In some embodiments, the generated dental preparation guide is such that it can be arranged in relation to a digital 3D representation of the pre-prepared or a prepared set of teeth with the validation surface facing the tooth. By visualizing a virtual dental preparation guide arranged in relation to the digital 3D representation often provide direct information to the dentist with respect to which portions of the tooth which needs to be further prepared.

In the context of the present invention, the phrase "pre-prepared set of teeth" is used in relation to a set of teeth prior to the preparation that the dental preparation is designed for validating. In some cases, a previous preparation has been performed to the pre-prepared set of teeth, such as a preparation of other teeth or a first preparation used for evaluating the health of the tooth for evaluating whether the entire tooth must be removed and replaced by a dental implant. In some embodiments, the physical dental preparation guide is manufactured by direct digital manufacturing such as by 3D printing or milling. With the continuous reduction in the acquisition costs for 3D printing and milling systems for dental applications, such equipment become attainable for the dentist and once the virtual dental preparation guide is created he may produce a physical guide in his consultation.

In the virtual case, the virtual dental preparation guide can be aligned with a digital 3D representation of the pre-prepared or the prepared set of teeth and virtual intersections of surface or distance between the surfaces can be used for the validation.

In the context of the present invention, the phrase "the dental preparation guide is configured to provide that . . . " is sometimes used as a short form of "the dental preparation guide is configured to provide that a preparation of the tooth according to the dental preparation guide will ensure that . . . ".

In the context of the present invention a prepared tooth can also be referred to as a tooth preparation.

In the context of the present invention a dental restoration is a classical fixed restoration such as inlays/onlays, veneers, crowns, bridges, implant-retained structures etc., but by analogy also removable restorations such as dentures.

In the context of the present invention a patient is the person for whom a restoration is designed. There may be medical indications for dental treatment of this patient, but also cosmetic considerations can be a relevant motivation for having a dental restoration designed.

In the context of the present invention, the surface provided by a Boolean addition of a first and a second surface may correspond to the surface of a solid structure formed by a logical disjunction of the solid structures with surfaces according to the first and second surface.

It is an advantage of the present invention that it provides an efficient control over the shape and position of the validation surface of the dental preparation guide on contrast to the prior art methods.

Further, the method of the present invention can create dental preparation guides which are capable of providing information about how adequate a validation of a tooth preparation is compared to prior art dental preparation guides.

In some embodiments, the method according to the present invention is a method which runs in parallel to a treatment of a patient. The method of generating and/or manufacturing the dental preparation guide may run in parallel with the dental work performed by the dentist on the patient's set of teeth, such as in parallel with the preparation of the tooth or teeth. The preparation of the tooth is hence not contemplated as part of the method.

According to an aspect of the invention is disclosed a method for generating a dental preparation guide configured for validating the preparation of at least one tooth for a dental restoration, said method comprising:

a: obtaining a digital 3D representation of a pre-prepared set of teeth;

b: virtually removing the at least one tooth from the digital 3D representation of the pre-prepared set of teeth, such that a digital 3D representation of a remaining set of teeth is formed;

c: providing a virtual target dental restoration expressing a target shape of the dental restoration;

d: creating a virtual validation surface for the dental preparation guide based on the virtual target dental restoration, where the validation surface is such that the preparation of the at least one tooth can be validated by the dental preparation guide; and e: creating a virtual preparation guide surface by combining the virtual validation surface and at least part of the surface of the digital 3D representation of the remaining set of teeth.

According to an aspect of the invention is disclosed a method for validating the preparation of at least one tooth for a dental restoration, said method comprising:

generating a virtual dental preparation guide configured for validating the preparation of the at least one tooth;

obtaining a digital 3D representation of the prepared set of teeth; and visualizing the virtual dental preparation guide together with the digital 3D representation of the prepared set of teeth.

In some embodiments, the combining of the virtual validation surface and at least part of the surface of the digital 3D representation of the remaining set of teeth comprises connecting the virtual validation surface and at least part of the surface of the digital 3D representation of the remaining set of teeth and thereby creating the virtual preparation guide surface.

One advantage of this approach is that the created virtual preparation guide surface has both the validation surface and a surface which can contact and rest on areas of the set of teeth which are not modified by the preparation.

In some embodiments, the target shape and/or the virtual target dental restoration is based on a designed virtual diagnostic wax-up, on a generic dental restoration selected from a library, or on the shape of the tooth in the digital 3D representation of the pre-prepared set of teeth. The target shape may be shaped substantially according to original shape of the set of teeth or it may be defined by modifying the digital 3D representation of the pre-prepared set of teeth.

An advantage of having a target shape which is based on the shape of the tooth in the digital 3D representation of the pre-prepared set of teeth is that the patient is used to the feel of the teeth which is maintained in this case.

An advantage of having a target shape which is based on a designed virtual diagnostic wax-up is that the appearance of the patient's set of teeth can be modified when the dental restoration is inserted at the prepared tooth.

In some embodiments, the target shape and/or the virtual target dental restoration is based on one or more aesthetic parameters. The aesthetic parameter may be selected from the shape of the individual teeth, the color of the teeth, or the relative arrangement of the teeth.

An advantage of this is that the target shape of the dental restoration can be designed according to the patient's wishes concerning the aesthetic appearance of his set of teeth.

In some embodiments, the virtual diagnostic wax-up is formed based on the digital 3D representation of the pre-prepared set of teeth, is selected from library, or is obtained by scanning a physical model of a diagnostic wax-up for the teeth.

In some embodiments, the virtual diagnostic wax-up is generated by combining teeth of a teeth template with the digital 3D representation of the pre-prepared set of teeth.

An advantage of a virtual diagnostic wax-up generated from both the teeth of a teeth template and the digital 3D representation of the pre-prepared set of teeth is that a true visualization of the expected outcome of the restorative work can be provided.

In some embodiments, the virtual diagnostic wax-up is generated by modifying at least a portion of the digital 3D representation of the pre-prepared set of teeth, where the modified portions relate to the tooth or teeth of the dental restoration.

In some embodiments, the design of the virtual diagnostic wax-up is such that the virtual diagnostic wax-up automatically is aligned with the digital 3D representation of the pre-prepared set of teeth and/or of the remaining set of teeth.

In some embodiments, the virtual diagnostic wax-up is designed in relation to a digital 3D representation of the set of teeth, such as the digital 3D representation of the pre-prepared or the prepared set of teeth, such that it is automatically aligned with the digital 3D representation of the remaining set of teeth. A target dental restoration defined from the diagnostic wax-up will then accordingly also be automatically aligned with the digital 3D representation of the remaining set of teeth and the virtual validation surface can directly be combined with the digital 3D representation of the remaining set of teeth.

In some embodiments, at least part of the virtual diagnostic wax-up is created using a tooth generating algorithm. Such an algorithm can be implemented on a computer.

In some embodiments, the virtual validation surface is created based on the virtual diagnostic wax-up. This may be via a target dental restoration based on the virtual diagnostic wax-up.

In some embodiments, the method comprises defining a 3D sectioning spline configured for virtually sectioning the digital 3D representation of the pre-prepared teeth into a part corresponding to the tooth and a part corresponding to the digital 3D representation of the remaining set of teeth.

One advantage of this is that the tooth part can be virtually removed and the digital 3D representation of the remaining set of teeth can be used for the generation of the virtual preparation guide surface without having the tooth part of the digital 3D representation of the pre-prepared set of teeth interfering with the design process.

In some embodiments, virtually removing the tooth comprises defining said 3D sectioning spline and virtually dividing the digital 3D representation of the pre-prepared teeth into a part corresponding to the tooth and a part corresponding to the digital 3D representation of the remaining set of teeth at the 3D sectioning spline.

Using a 3D sectioning spline provides the advantage that an operator can define the spline himself and thereby determine where the tooth part and the remaining set of teeth are separated.

The 3D sectioning spline may be defined automatically using a computer implemented sectioning spline generating algorithm. The operator can inspect the location of the 3D sectioning spline relative to the digital 3D representation of the pre-prepared set of teeth before approving the removal of the tooth at this spline.

In some embodiments, the method comprises manually defining the 3D sectioning spline or manually adjusting an automatically generated 3D sectioning spline.

In some embodiments, manually defining the 3D sectioning spline or manually adjusting an automatically generated 3D sectioning spline is based on sectioning spline control points used to control the shape of the 3D sectioning spline. Such control points has the advantage that the operator can adjust the 3D sectioning spline using a pointing tool such as a computer mouse.

In the sectioning of the digital 3D representation, the 3D sectioning spline may be defined to follow the gingival edge at the tooth.

One advantage of this is that in the digital 3D representation of the remaining set of teeth the tooth surface is completely removed and the created virtual validation surface can be shaped to not have any portions corresponding to the tooth surface. The created virtual preparation guide surface can then have a shape which corresponds to a removal of teeth material over the entire tooth surface such as often is preferred when preparing the tooth for a crown restoration.

At least a portion of the 3D sectioning spline for a tooth may be configured to be shaped according to an expected shape of the preparation line that is provided when the tooth is prepared. That is, in both the case where the 3D sectioning spline is automatically generated and when it is defined manually it may be arranged to follow a path along which the operator plans to define the preparation line of a tooth.

One advantage of this is that the dental preparation guide can be designed to assist the dentist in placing the preparation line correctly.

In some embodiments, the virtually sectioning of the portion of the digital 3D representation corresponding to the tooth is such that this portion can be virtually separated from the digital 3D representation of the pre-prepared teeth and can be moved away or deleted from this.

It can be an advantage that when viewing the digital 3D representation of the remaining set of teeth and the virtual surfaces of the dental preparation guide that the removed tooth no longer is visible.

In some embodiments, the tooth is virtually removed from the digital 3D representation of the pre-prepared set of teeth by virtually separating the part corresponding to the tooth from the part corresponding to the remaining set of teeth. The tooth part may still be arranged in the same position of the digital 3D representation of the set of teeth as before it was removed but the removed part is not included in the remaining set of teeth.

It may also possible to omit the step of virtually removing the tooth as long as its surface is made distinguishable from the remaining part of the set of teeth. This could for instance be done by adding information to the surface of the otherwise virtually removed tooth. In the visualization of the virtual preparation guide surface or the virtual dental preparation guide, the tooth could then be presented as a highly or at least slightly transparent surface. A 3D remaining teeth spline can then be formed in relation to the digital 3D representation of the pre-prepared set of teeth which has the tooth visualized differently.

The 3D sectioning spline can be used to define a tooth which subsequently can be virtually separated or virtually moved away from the digital 3D representation of the pre-prepared teeth.

When several teeth are virtually removed, the 3D sectioning spline may virtually section the digital 3D representation of the prepared teeth into a part corresponding to these teeth and a part corresponding to the remaining set of teeth.

In some embodiments, the 3D sectioning spline substantially follows a boundary between the virtual target dental restoration and the digital 3D representation of the pre-prepared set of teeth.

Virtually removing the tooth may introduce a virtual hole in the digital 3D representation of the remaining set of teeth. The virtual hole may comprise a gingival hole and interproximal holes at the neighboring teeth if these are still present in the digital 3D representation of the remaining set of teeth. The virtual hole may be bounded by the 3D sectioning spline.

In some embodiments, the method comprises creating a virtual replacement surface configured for at least partly closing the virtual hole, such as substantially closing the virtual hole. The virtual replacement surface may be a generic surface selected from a library or a surface generated using curvature-based hole closing algorithms. In some embodiments, the virtual replacement surface comprises a virtual gingival surface, such as a virtual gingival. In some embodiments, the virtual replacement surface comprises a virtual tooth preparation.

One advantage of creating such a virtual replacement surface is that this surface can be used when defining an interproximal section of a 3D remaining teeth spline.

In some embodiments, the method comprises defining a 3D remaining teeth spline.

In some embodiments, at least a section of the 3D remaining teeth spline is configured to follow a boundary of the virtual hole introduced in the digital 3D representation of the remaining set of teeth by virtually removing the tooth.

Defining a 3D remaining teeth spline has the advantage that this spline can mark the location where the digital 3D representation of the remaining set of teeth connects to virtual surfaces used when generating the virtual preparation guide surface.

In some embodiments, the 3D remaining teeth spline is defined from the 3D sectioning spline, such that at least a section of the 3D remaining teeth spline is shaped substantially according to the 3D sectioning spline.

This has the advantage that the dentist or dental technician often prefers that at least some sections of the 3D remaining teeth spline has the same shape as the spline he used for sectioning the digital 3D representation of the pre-prepared set of teeth.

In some embodiments, the 3D remaining teeth spline comprises a lingual part and/or a buccal/labial part and/or an interproximal part. The lingual part and the buccal/labial part of the 3D remaining teeth spline may be configured to follow the boundary of the virtual hole at the lingual and the buccal portion of the set of teeth, respectively.

In some embodiments, the lingual part and/or a buccal/labial part of the 3D remaining teeth spline is substantially identical to the 3D sectioning spline over the corresponding parts of the digital 3D representation of the pre-prepared set of teeth.

In some embodiments, the 3D remaining teeth spline comprises an interproximal part. The interproximal part is preferably defined by modifying the 3D sectioning spline. In some cases a section of the 3D sectioning spline follows the interproximal boundary between of the tooth which is to be virtually removed and its neighboring tooth in such a manner that the 3D sectioning spline moves away from the gingival. When defining the 3D remaining teeth spline by modifying the 3D sectioning spline this section of the 3D sectioning spline may be shaped to follow the gingival at the interproximal portion of the tooth.

This has the advantage that the 3D remaining teeth spline is shaped in a manner which resembles the anatomical situation such that when the virtual preparation guide surface is defined by connecting the digital 3D representation of the remaining set of teeth at the 3D remaining teeth spline the created surface has a more homogeneous shape compared to the case where the 3D remaining teeth spline is identical to the a 3D sectioning spline which at the interproximal parts is far away from the gingiva.

In some embodiments, the interproximal part of the 3D remaining teeth spline is arranged such that it divides at least a portion of said virtual hole into an interproximal hole and a gingival hole.

In some embodiments, the interproximal part of the 3D remaining teeth spline is arranged such that it follows the virtual replacement surface and divides at least a portion of said virtual replacement surface into an interproximal virtual surface and a gingival virtual surface.

In some embodiments, the 3D remaining teeth spline is defined in relation to this virtual replacement surface. The 3D remaining teeth spline may be arranged to divide the virtual replacement surface into the virtual gingival surface and one or two virtual interproximal surfaces depending on whether the neighboring teeth still are present in the digital 3D representation of the remaining set of teeth.

In some embodiments, the method comprises creating a virtual gingival surface configured for closing at least part of the gingival hole in the digital 3D representation of the remaining set of teeth.

This surface can be used when defining other surfaces or splines used in the method, or for digitally designing the dental restoration, such as for designing a pontic of a bridge restoration.

In some embodiments, the method comprises creating a virtual interproximal surface configured for closing at least part of the interproximal hole in the digital 3D representation of the remaining set of teeth.

The virtual gingival surface and/or the virtual interproximal surface may be created using a curvature based hole-closing algorithm.

In some embodiments, the method comprises making the virtual gingival surface and/or the virtual interproximal surface and/or the virtual replacement surface part of the digital 3D representation of the remaining set of teeth. The making may comprise connecting the virtual gingival surface and/or the virtual interproximal surface and/or the virtual replacement surface with the digital 3D representation of the remaining set of teeth. The surfaces may be connected with the digital 3D representation of the remaining set of teeth by a lofting process.

For the virtual gingival surface, this may correspond to virtually replacing the virtually removed tooth with the virtual gingival surface in the digital 3D representation of the remaining set of teeth. This surface can e.g. be used in designing the dental restoration, such as when designing a pontic of a bridge restoration.

In some embodiments, the virtual validation surface is shaped according to the virtual target dental restoration. Validation using the dental preparation guide may then comprise estimating the difference between a pre-prepared shape of the tooth and the shape of the target dental restoration. Such a dental preparation guide may be useful in cases where the target dental restorations differs significantly from the shape of the teeth in the pre-prepared set of teeth as this dental preparation guide may give the dentist an indication of how far the tooth is from the shape according to the diagnostic wax-up and hence where and how much tooth material must be removed. The tooth must then be prepared further than the validation surface and e.g. the available space for the dental restoration must be estimated from the space between the validation surface and the surface of the prepared set of teeth.

In some embodiments, the method comprises creating a virtual minimum preparation surface. The virtually removed tooth can then be virtually replaced with the virtual minimum preparation surface in the digital 3D representation of the remaining set of teeth. The virtual minimum preparation surface may show the maximum size of the prepared tooth, i.e. a boundary within the prepared tooth has to be confined in order to ensure that sufficient space is provided for the dental restoration.

In some embodiments, the virtual minimum preparation surface of the tooth is determined from the virtual target dental restoration. The virtual minimum preparation surface is then shaped such that a tooth prepared according to this surface is ready for accepting a dental restoration shaped according to the target dental restoration.

In some embodiments, the virtual minimum preparation surface of the tooth is determined by offsetting at least a part of the surface of the virtual target dental restoration inwards. The size of the offset may be uniform or change over the tooth surface, such that the offset e.g. is larger at the occlusal end of the prepared tooth. The offset may be determined from parameter values entered by an operator or from predefined values of such parameters.

One advantage of determining the virtual minimum preparation surface by such an offset is that the offset directly provides a measure of a minimum thickness of the dental restoration such that the mechanical stability of the dental restoration and e.g. its capability with respect to changing color can be taken into account.

In some embodiments, the virtual validation surface is designed such that tooth material must be removed from areas which in fact are within the minimum preparation surface. This may be done to ensure that the surface of the prepared tooth is rough in these areas such that the dental restoration will adhere better to the prepared tooth.

In some embodiments, the virtual validation surface is modified to provide that the created virtual dental preparation guide follows the surface of the tooth in regions where the virtual validation surface otherwise would be located outside the tooth. This may e.g. be done when a virtual minimum preparation surface of the tooth is formed by an offset of the virtual target dental restoration, and a portion of the virtual minimum preparation surface extends outside the tooth. The portions of the offset surface which extends beyond the tooth are then virtually pushed onto the tooth surface or virtually cut to the tooth surface. For a physical dental preparation guide, the pushed sections can the rest on the relating surface of the prepared tooth and thus provide that the dental preparation guide is supported in its correct arrangement relative to the patient's set of teeth.

In some embodiments, the properties of the material in which the dental restoration is to be manufactured are taken into account, such as taken into account when determining the virtual minimum preparation surface. The minimum thickness and critical angles for the dental restoration depends on the material. When taking the material properties into account, the dental restoration can be designed to have some desired mechanical and color changing properties and the tooth can be prepared to accept a restoration which is designed to fulfill the requirements to these properties.

The minimum thickness of the wall of the restoration depends on the material of the restoration. One minimum thickness is for example required to provide a robust design of the dental restoration when the restoration is made in gold while another minimum thickness is needed when it is made in a ceramic.

The shape of the prepared tooth is preferably also adjusted to match the material of the restoration. A restoration made from gold can have a tapered finishing towards the preparation line of the prepared tooth while a ceramic restoration often requires a more abrupt termination.

In some embodiments, the generation of the dental preparation guide takes into account these matters such that the dental preparation guide is configured for guiding the drill to provide a prepared tooth at which a restoration having a tapered or abrupt finishing can be arranged.

In some embodiments, the virtual minimum preparation surface and/or the virtual validation surface is such that a volume for cement is provided between the prepared tooth and the dental restoration when the dental restoration is arranged at the patient's teeth. This has the advantage that the cement can be applied to the tooth/dental restoration without further grinding material away.

In some embodiments, a virtual preparation line is defined in relation to the virtual validation surface.

In some embodiments, the virtual validation surface is based on the virtual minimum preparation surface. In such cases, the virtual preparation line can be defined in relation to the virtual minimum preparation surface.

In some embodiments, the virtual preparation line is defined on the virtual validation surface and corresponds to a virtual equivalent of a preparation line defined by preparing the actual tooth.

In some embodiments, the virtual preparation guide surface is created by virtually connecting the virtual minimum preparation surface and the digital 3D representation of the remaining set of teeth, i.e. the virtual minimum preparation surface and the digital 3D representation of the remaining set of teeth are combined by connecting these surfaces. In this case at least a part of the virtual validation surface is substantially identical to the virtual minimum preparation surface.

In some embodiments, the virtual minimum preparation surface is represented by a virtual minimum preparation. In a user interface according to the present invention, such a virtual minimum preparation can be visualized together with the digital 3D representation of the remaining set of teeth such that the operator can evaluate how good the minimum preparation will be with respect to the preparation process and with respect to inserting the manufactured restoration.

In some embodiments, the virtual preparation guide surface is shaped according to the virtual minimum preparation. Some portions of the virtual preparation guide surface may be configured to follow the virtual minimum preparation closely while at other portions, such as when a safety zone is desirable, the virtual preparation guide surface may deviate from the virtual minimum preparation.

In some embodiments, the virtual preparation guide surface at least in part is created by a Boolean addition of the virtual minimum preparation surface and the digital 3D representation of the remaining set of teeth.

In this approach the virtual preparation guide surface can easily be generated once the virtual minimum preparation surface and the digital 3D representation of the remaining set of teeth are arranged relative to each other in a way that an operator finds appropriate. For an implementation of the method presented to the operator in a user interface, the user interface can have a window showing the virtual minimum preparation surface and the digital 3D representation of the remaining set of teeth and a virtual button which when activated performs the Boolean addition. The operator may be able to move adapt the virtual minimum preparation surface and/or move it relative to the digital 3D representation of the remaining set of teeth using e.g. a computer mouse to perform these actions on the virtual minimum preparation surface in said window.

In some embodiments, the virtual preparation guide surface at least in part is created by a Boolean addition of the virtual validation surface and the digital 3D representation of the remaining set of teeth. The comments provided above in relation to the Boolean addition of the virtual minimum preparation surface and the digital 3D representation of the remaining set of teeth also applies here for the Boolean addition of the virtual validation surface and digital 3D representation of the remaining set of teeth.

In some embodiments, the method comprises generating a connecting surface configured for connecting the virtual validation surface and the digital 3D representation of the remaining set of teeth.

The connecting surface may close holes in the virtual preparation guide surface located between the virtual validation surface and the digital 3D representation of the remaining set of teeth, such that a coherent virtual preparation guide surface is created.

In some embodiments, the connecting surface is configured to connect to the digital 3D representation of the remaining set of teeth at the 3D remaining teeth spline. This approach has the advantage that an operator can determine, via the shape of the 3D remaining teeth spline, how the created virtual preparation guide surface is shaped at the digital 3D representation of the remaining teeth. Further, the operator can determined where the virtual preparation guide surface is shaped according to the digital 3D representation of the remaining teeth and where it is shaped according to the virtual validation surface.

In some embodiments, generating the connecting surface comprises a lofting process. Lofting can be applied to connect two surfaces by a new surface. A lofting process may comprise fitting a parametric surface to a boundary of one surface and to a boundary of a second surface. The lofting process may be used to define a connecting surface configured to connect the virtual validation surface with the digital 3D representation of the remaining set of teeth.

In some embodiments, the formation of the connecting surface is computer controlled or computer assisted.

In some embodiments, the method comprises defining a 3D validation surface spline in relation to the virtual validation surface, where the connecting surface is configured to connect to the virtual validation surface at the 3D validation surface spline.

Using a 3D validation surface spline to determine where the connecting surface is configured to connect to the virtual validation surface has the advantage that the operator can decide whether to e.g. connect to the virtual validation surface above a virtual preparation line of the virtual validation surface such that a safety zone is defined.

In some embodiments, the 3D validation surface spline is automatically defined using a computer implemented algorithm.

One advantage of this is that the computer implemented algorithm can define the 3D validation surface spline faster than the operator.

In some embodiments, the 3D validation surface spline is manually defined or adjusted using virtual control points visualized in combination with a visualization of the diagnostic wax-up.

One advantage of this is that the operator is allowed to define the 3D validation surface according to his personal preferences.

In some embodiments, the 3D validation surface spline is configured to substantially follow the virtual preparation line.

In some embodiments, the 3D validation surface spline is located above the virtual preparation line, i.e. the 3D validation surface spline is closer to the occlusal plane of the tooth than the virtual preparation line is.

In some embodiments, a computer implemented hole-closing algorithm is applied in the hole closing and/or in generating the connecting surface.

One advantage of this is that the computer implemented hole-closing algorithm can virtually close the hole and/or generating the connecting surface faster than an operator.

One way of performing a lofting process is to first determine a correspondence between the vertices at the two boundaries that are to be connected by the generated surface. The correspondence may be determined by an exhaustive search for the correspondence that yields the lowest average distance between the corresponding vertices under the constraint that the order of the vertices is preserved. The loft may be based on a cubic B-spline surface, which requires a number of control points to be specified. For each vertex is calculated the vector, $v_c$, which is perpendicular to the vertex normal and the boundary orientation vector in the vertex. The vertex normal is calculated as the area weighted average of the triangle normals of the triangles connected to the vertex. For each vertex in the set of corresponding vertices two control points are created as the vertex $\pm v_c$. An additional control point is then created as $v_{c1}$ and $v_{c2}$ added to the midpoint between the corresponding vertices $p_1$ and $p_2$. Beside the created control points the two vertices also act as control points. When this process has been repeated for all sets of corresponding vertices, the surface is fully defined by the controls points. New vertices are then sampled on the surface, i.e. by sampling the vertices on the spline, which connect the corresponding vertices. Given these vertices and the ordering of the corresponding vertex sets, the neighbor relationships between the sampled vertices are known. Knowing these relationships makes it straightforward to connect the neighboring vertices by triangles. When the loft has been applied it is not ensured that the e.g. the virtual validation surface is not penetrated by the connecting surface. This penetration can however be minimized by moving the control points behind the virtual validation surface, such as by moving the additional control point between the corresponding vertices backward along $v_{c1}$ and $v_{c2}$ until it is behind the virtual validation surface.

In some embodiments, the virtual preparation guide surface is configured to define a safety zone at the virtual preparation line and/or at the 3D sectioning spline, where said safety zone provides a distance between the digital 3D representation of the remaining set of teeth and the virtual preparation guide surface.

The safety zone may hence provide space in which the dentist is allowed to select between different locations of the preparation line for the tooth and/or of the preparation margin line relative to the gingival. The safety zone can also ensure that the dental preparation guide does not contact the sensitive parts of the gingiva when placed at the patient's teeth. A safety zone may be realized when the 3D validation surface spline is located above the virtual preparation line. In this case, the virtual preparation guide surface is locally offset away from the virtual preparation line whereby the space of the safety zone is provided.

In some embodiments, the dental preparation guide is manufactured by direct digital manufacturing such as by 3D printing or milling In some embodiments, the dental preparation guide is manufactured by forming a physical model of the set of teeth in which the tooth is prepared according to the virtual validation surface, and shaping the material of the dental preparation guide according to this physical model.

Shaping the material of the dental preparation guide may comprise vacuum forming the material onto the physical model. This approach has the advantage that while only very few biocompatible materials can be used for direct digital manufacture there many biocompatible materials which can be vacuum formed onto a solid model.

In some embodiments, the generated virtual dental preparation guide comprises a shelled virtual preparation guide surface.

One advantage of shelling the virtual preparation guide surface is that the surface itself not necessarily can be used for direct digital manufacture while a virtual model defined by the shelling of the surface is suitable for such manufacture.

In some embodiments, the method comprises shelling at least a selected part of the virtual preparation guide surface such that the virtual dental preparation guide comprises an inner shell surface and an outer shell surface in the selected part.

In some embodiments, the virtual preparation guide surface and/or the virtual validation surface is parameterized by a number of vertices, where the vertices are connected by triangles.

In some embodiments, the outer shell surface is shaped according to the virtual validation surface.

In some embodiments, the outer shell surface is shaped according to the created virtual preparation guide surface and the shelling defines the inner shell surface from the outer shell surface. In this case, the shelling may comprise offsetting inwardly a copy of each vertex in the outer shell surface, removing the number of copied vertices being closer to the outer shell surface than a given minimum shell thickness, and creating the inner shell surface by triangulation of the remaining copied vertices.

When the outer shell surface is shaped according to the created virtual preparation guide surface, the outer shell surface may be according to the target shape of the dental restoration.

In some embodiments, an intermediate physical model is manufactured from the shelled virtual preparation guide surface using direct digital manufacturing. The dental preparation guide can then be manufactured by shaping the material of the dental preparation guide using said intermediate physical model. The inner surface and outer surfaces of the intermediate physical model may be defined by the inner shell surface and the outer shell surface, respectively.

The outer surface of the intermediate physical model can be shaped according to the virtual preparation guide surface and the manufacture of the dental preparation guide can be such that the inner surface of the manufactured dental preparation guide is shaped according to the outer surface of the intermediate physical model. The inner surface of the manufactured dental preparation guide then corresponds to a negative of the virtual preparation guide surface and the dental preparation guide fits onto a tooth prepared according to the virtual preparation guide surface. If the tooth is prepared event further, a gap is present between the inner surface and the dental preparation guide and the tooth surface when the dental preparation guide is arranged at the patient's set of teeth.

This approach has the advantage that while only very few biocompatible materials can be used for direct digital manufacture there many biocompatible materials which can be vacuum formed onto such an intermediate physical model.

In some embodiments, shaping the material of the dental preparation guide using said intermediate physical model comprises vacuum forming the material of the dental preparation guide onto the intermediate physical model.

In some embodiments, the dental preparation guide is such that the inner shell surface is shaped according to the virtual validation surface.

In some embodiments, the inner shell surface is shaped according to the virtual preparation guide surface and the shelling defines the outer shell surface from the inner shell surface. The inner shell surface may be the surface which faces the set of teeth when the dental preparation guide is arranged at the teeth while the outer shell surface is facing the surrounding buccal, labial and lingual tissue and the antagonist.

When the virtual preparation guide surface and/or the virtual validation surface is part of an inner shell surface the shelling may provide an outer shell surface. In this case, the shelling may comprise offsetting outwardly a copy of each vertex in the inner shell surface, removing the number of copied vertices being closer to the inner shell surface than a given minimum shell thickness, and creating the outer shell surface by triangulation of the remaining copied vertices.

This approach has the advantage that the dental preparation guide can be manufactured directly without the need for an intermediate physical model.

In some embodiments, the dental preparation guide is manufactured from said shelled virtual preparation guide surface using direct digital manufacturing. This may be the case when the inner shell surface is shaped according to the virtual preparation guide surface Shelling may expand the virtual preparation guide surface to become a shell with a finite thickness. For many devices it is beneficial or crucial that a minimum shell thickness is guaranteed.

In one shelling algorithm configured for providing a shell based on an outer shell surface, the first step is to create a copy of each vertex in the outer shell surface. A new vertex on the inner shell is created along a scaled normal of the corresponding vertex in the outer shell surface. The vertex normal is calculated as the average of the normals of the connected triangles weighted by their area. If the minimum shell thickness has to be ensured it is not sufficient to offset the vertex with the specified shell thickness. However the offset, which locally ensures the shell thickness, can be found as the maximum scale factor, which projects the scaled version of the vertex normal onto the full length of the triangle normals scaled by the predefined thickness. Only the normals of the triangles connected to the vertex are of relevance. Unfortunately, the proposed offsetting only ensures a local shell thickness. In areas with convex surfaces and high curvature the offset vertices tend to violate the minimum shell thickness. These violating vertices are removed in a second step to ensure a proper shell thickness. Finally, the new inner shell may then be created by a triangulation of the created vertices. The triangulation may be performed using a standard 3D triangulation method such as proposed by Hoppe et al. in "Surface Reconstruction from unorganised points", Computer Graphics, 26(2), 1992, pp. 71-78.

In some embodiments, the dental preparation guide is generated in such a manner that it can be arranged relative to the patient's set of teeth with the validation surface facing the tooth. The tooth may be that of the pre-prepared set of teeth or the prepared tooth.

A base may be provided to the shelled virtual preparation guide surface prior to the manufacture of the physical dental preparation guide. The base may be located at the occlusal portion of the outer shell surface.

A base may be provided to the shelled virtual preparation guide surface prior to the manufacture of the intermediate physical model. The base may be located at the cervical portion of the shelled surface.

The validation surface is configured to validate the preparation of one or more teeth in the set of teeth. In some embodiments, such as when the validation surface is according to a minimum preparation of the tooth, an insufficient preparation of the tooth will prevent the dental preparation guide from reaching a target position relative to the set of teeth. If the preparation is sufficient and there are no other teeth which requires (further) preparation, the dental preparation guide may be moved into the target position. If the dental preparation guide is manufactured in a relative soft material it may still be possible for the dental preparation guide to reach the target position even with an insufficient preparation of the tooth, but then a resistance is experienced.

In some embodiments, the method comprises determining an insertion direction for the dental restoration and where the insertion direction is taken into account when creating the virtual validation surface, such that e.g. the virtual minimum preparation surface may be based on the insertion direction.

In some embodiments, taking into account the insertion direction comprises ensuring that the virtual validation surface is configured to provide that undercuts at the prepared tooth are reduced or avoided if the tooth is prepared according to the virtual validation surface, such as according to the validation surface of a physical dental preparation guide manufactured based on the virtual dental preparation guide. In some embodiments, the undercuts are reduced or avoided by trimming the virtual validation surface.

In the context of the present invention, the phrase "undercuts at the prepared tooth" may refer to undercuts seen relative to the dental restorations path along the insertion direction as illustrated in FIG. 8, where the dental restoration cannot be arranged at the prepared tooth due to such an undercut.

In some embodiments, the method comprises generating an undercut-free virtual surface from the virtual minimum preparation surface and the virtual validation surface is created based on the undercut-free virtual surface. The undercut-free surface can be generated using a virtual block-out tool configured for blocking out undercut regions in the digital 3D representation of the pre-prepared or prepared set of teeth.

In some embodiments, a downwards taper is provided to the virtual minimum preparation surface and/or to the undercut-free virtual surface, where the taper is from the virtual preparation line to the occlusal surface of the tooth with a taper angle. The taper angle may be in the range of about 0.5 degrees to about 15 degrees, such as in the range of about 1 degree to about 10 degrees, such as in the range of about 2 degrees to about 5 degrees.

In some embodiments, the dental restoration comprises a bridge restoration, single crown, a temporary restoration, or a removable partial denture In some embodiments, the dental restoration comprises a bridge restoration and the dental preparation guide is configured for validating the preparation of two or more teeth for accepting the crown parts of the bridge restoration.

In some embodiments, the dental restoration comprises a removable partial denture and the dental preparation guide is configured for validating the preparation of two or more teeth prepared for securing the partial denture in the patient's mouth.

In some embodiments, the dental preparation guide is configured for validating the preparation of two or more teeth. In this case, one or more teeth may virtually be removed from the digital 3D representation of the pre-prepared set of teeth such that the remaining set of teeth lacks one or more teeth compared to the pre-prepared set of teeth. The 3D Sectioning spline may be defined for each tooth or for two or more teeth. Some teeth in the digital 3D representation of the pre-prepared set of teeth may then be virtually replaced by a virtual minimum preparation or a virtual gingival surface in the digital 3D representation of the remaining set of teeth. A virtual diagnostic wax-up for a bridge restoration may e.g. be designed based on a template selected from a library.

In some embodiments, the dental preparation guide is configured to be used in relation to a first region and a second region of the set of teeth, where said first region comprises the teeth relating to the dental restoration, and said second region comprises at least one additional tooth, where the second region is used for aligning the dental preparation guide correctly relative to the set of teeth.

If the dental restoration is a bridge restoration for the anterior maxillary teeth with a pontic for the 8-tooth and the 9-tooth, and crowns of the bridge attached to the 7-tooth and the 10-tooth, the first region comprises teeth 7-10 while the second region can comprise the 6-tooth and the 11-tooth or teeth further away from the 7-10 teeth. The teeth are numbered according to the universal tooth designation system. In this case, the dental preparation guide is hence configured for engaging not only the prepared teeth but also at least one other tooth which then ensures that the dental preparation guide is aligned correctly relative to the pre-pared teeth. A manufactured dental preparation guide may then be configured for being arranged in relation to both the teeth of the first and the second region. The alignment of the dental preparation guide is provided on the teeth of the second region, while the dental preparation guide validates the preparation of the 7-tooth and the 10-tooth. The 8-tooth and the 9-tooth may already have been extracted prior to the validation of the preparation of the 7-tooth and the 10-tooth. Alternatively or in addition to using the neighbor teeth to support the dental preparation guide the gingiva can be used for this purpose and the corresponding part of the digital 3D representation of the remaining set of teeth is included when generating the virtual preparation guide surface.

In some embodiments, at least one aperture is defined in the shelled virtual preparation guide surface of the dental preparation guide such that when the manufactured dental preparation guide is arranged in relation to the patient's set of teeth, the aperture provides access to an area of the tooth. The tooth may be the prepared or the pre-prepared tooth. A pointed tool may then enter though the aperture of the manufactured dental preparation guide and measure the distance from the dental preparation guide to the surface of the tooth. This can for example be utilized when the validation surface of the dental preparation guide is shaped according to a diagnostic wax-up, since it allows the dentist to measure whether the space provided for the dental restoration by the preparation of the tooth is sufficiently large such that a robust dental restoration can be made.

In some embodiments, the validation surface is configured to validate the preparation of at least one surface of the tooth or teeth, such as the buccal, the lingual, the occlusal or an inter-proximal surface of the tooth or teeth. In some embodiments, the validation surface is configured to validate the preparation of the entire surface of the tooth.

In one embodiment, the method comprises creating an intermediate version of the minimum preparation surface. The intermediate version may be shaped according to an eggshell configuration, where the eggshell configuration can be defined by offsetting at least part of the surface of the virtual target dental restoration inwards thus forming an inner shell surface.

The tooth preparation, physical or virtual, may be configured such that the restoration will provide the desired aesthetic appearance. That is the preparation is adapted to provide that the dental restoration may have the desired shape, placement and color.

In some embodiments, the virtual target dental restoration and the digital 3D representation of the remaining set of teeth are aligned at the 3D sectioning spline. If there is a gap between the two, this gap may be closed using hole-closing algorithms, such as a curvature based hole-closing algorithm or via a connecting surface configured to connect the virtual target dental restoration to the digital 3D representation of the remaining set of teeth.

In some embodiments, the method comprises combining the virtual minimum preparation and the gingival portion of the virtual validation surface. If there is a gap between the two, this gap may be closed using hole-closing algorithms, such as a curvature based hole-closing algorithm.

In some embodiments, the method comprises aligning the virtual validation surface and/or the virtual minimum preparation with the digital 3D representation of the remaining set of teeth. The virtual validation surface and the digital 3D representation of the remaining set of teeth may be automatically aligned when the virtual validation surface is generated from a virtual diagnostic wax-up which is aligned with the digital 3D representation of the remaining set of teeth.

In some embodiments, the method comprises that information relating to the size and/or shape of the drill used for preparing the tooth is provided and generating the dental preparation guide takes into account said information.

In some embodiments, the dental preparation guide is generated without taking into account the information, and where an estimated shape of the prepared tooth is visualized, where the estimated shape is derived taking into account the information.

In some embodiments, the method comprises modifying the dental restoration such that it can be accepted by the prepared tooth. This may e.g. be the needed when the dentist is unable to prepare the tooth according to the dental preparation guide. In some cases a minor change in the dental restoration can solve the problem and ensure that the dental restoration can be accepted by the prepared tooth.

In some embodiments, the method comprises visualizing the virtual target dental restoration in relation to the digital 3D representation of the remaining set of teeth. This has the advantage that the dentist and the patient can evaluate of the aesthetic appearance of the teeth when the dental restoration is inserted in the patient's mouth.

In some embodiments, the method comprises generating a virtual structure with a surface which is traced out by translating the virtual preparation line along the insertion direction.

In some embodiments, the virtual validation surface is created based on the virtual structure, such that the virtual validation surface takes into account the insertion direction.

This has the advantage that the manufactured dental restoration can be inserted at the tooth prepared according to the dental preparation guide.

In some embodiments a downwards taper is provided to the virtual structure from the virtual preparation line to the occlusal surface of the tooth with a taper angle, such that the virtual structure may be shaped as a frustrum.

If the insertion direction is ignored, an undercut surface may be generated on the tooth appear even when the tooth is prepared according to the validation surface.

In some embodiments, the method comprises generating an undercut-free virtual surface from the virtual minimum preparation surface and the virtual structure. In some embodiments, the validation surface is created based on the undercut-free virtual surface. The undercut-free surface may be such that small undercuts below a specified size are accepted.

This has the advantage that a preparation shaped according to the validation surface will have no undercut regions (relative to the insertion direction) and the dental restoration can be arranged at the prepared tooth.

In some embodiments, the undercut-free virtual surface corresponds to the surface of virtual solid structure formed by a Boolean addition of the virtual structure and a solid structure with a surface according to the virtual minimum preparation surface.

In some embodiments, the digital 3D representation is provided by intra-oral 3D scanning of the set of teeth, or 3D by scanning a physical model or an impression of the set of teeth.

In some embodiments, the 3D scanning is performed by means of laser light scanning, white light scanning, probe-scanning, X-ray scanning, and/or CT scanning.

In some embodiments, the digital 3D representation comprises at least part of the gingival.

The digital 3D representation can be either point clouds, surface (faceted/meshed), or volumetric. Faceted/meshed models are sometimes preferred over point clouds, but faceted/meshed models can be generated from point clouds, for example by triangulation. Volumetric models can be obtained with a scanner applying penetrating radiation, such as CT scanners.

Some initial preparation may have been performed on the teeth of the pre-prepared set of teeth. The method may for example be one step in an iterative procedure for preparing the patient's set of teeth, such that the shape of the tooth in the pre-prepared set of teeth may be an intermediate shape as seen in a scanning of tooth which has been exposed to an initial preparation in a prior step of the procedure.

In some embodiments, the pre-prepared set of teeth corresponds to the patient's set of teeth prior to any preparation.

The set of teeth may comprise all the patient's teeth or a part of the patient's teeth.

In some embodiments, the digital 3D representation of the prepared set of teeth is obtained by scanning a prepared region comprising the prepared tooth, and merging the digital 3D representation obtained from the scan of the prepared region with a previously obtained digital 3D representation of the pre-prepared set of teeth. This has the advantage that a full scan is not required when scanning the prepared set of teeth and such that time can be saved. The portion of the digital 3D representation of the pre-prepared set of teeth corresponding to the prepared region may deleted or be made distinguishable from the prepared set of teeth, such that in effect this portion is replaced by the digital 3D representation of the prepared region.

In some embodiments, one or more parameters relating to the dental restoration are taken into account when generating the dental preparation guide. The one or more parameters may be selected from the group of minimum thickness of the walls of the restoration, the material or materials of the restoration, access for a drill to prepare the tooth, or the insertion direction of the dental restoration.

In some embodiments, the virtual dental preparation guide used for validating the preparation of a tooth is generated using the method for generating a dental preparation guide according to the present invention.

The validating of the tooth preparation may comprise confirming that the shape of the prepared tooth is such that said dental restoration can be realized and can be inserted at the prepared tooth. The validating may be based on one or more parameters relating to the dental restoration.

In some embodiments, the method comprises validating that the tooth may be prepared according to the virtual preparation guide surface.

In some embodiments, the digital 3D representation of the prepared set of teeth is obtained by a scanning in the mouth of the patient with an intra-oral scanner. The digital 3D representation of the prepared set of teeth may then be visualized together with the virtual dental preparation guide, such as visualized together with the virtual preparation guide surface while the patient still is in the dental chair.

It can be an advantage that the dentist can perform a validation of a tooth preparation by using an intra-oral scanner simultaneously or concurrently with the preparation procedure. He can scan a region where he has been preparing a tooth and by comparing the digital 3D representation of the region obtained by this scan of this region with the virtual dental preparation guide the dentist can see if he has cut away enough material of the tooth or if he needs to cut away more material, and where on the tooth the material should be removed from. This intra-oral scanning validation procedure can be an alternative and/or an addition to using physical preparation guides In some embodiments, the dental preparation guide is designed such that a drill can approach and engage the tooth when the dental preparation guide is arranged at the teeth. The drill may have a diameter corresponding to the desired thickness of the restoration at this particular part of the restoration, such that in an area of the tooth where e.g. 2 mm tooth material is to be removed, the dental preparation guide makes space for a 2 mm drill.

In some embodiments, the dental preparation guide is configured for guiding a dentist or a dental preparation machine in the preparation of the tooth.

For some teeth, such as a molar tooth, the removal to tooth material at the lingual, the buccal/labial surface, and/or at the occlusal surface can result in edges at the cusp of the tooth.

For some restoration materials, such as ceramics, it may be preferred that sharp edges are avoided. In some embodiments, the validation surface of the dental preparation guide is configured such that the surface of the prepared tooth has no such sharp edges. This may be achieved by smoothing transitions between e.g. the prepared lingual and occlusal surfaces of the tooth.

In some embodiments, the method for validating the preparation of a tooth comprises determining the distance between the digital 3D representation of the prepared set of teeth and the virtual validation surface or the virtual dental preparation guide at one or more selected locations on the tooth surface. Here it is contemplated that the dental preparation guide, either virtually or physically, is arranged at the tooth when the distance is measured. That is, the distance may be determined when the dental preparation guide is arranged in a target position in relation to the teeth. In some cases, the method comprises determining a minimum distance where the measured distance between the dental preparation guide and the prepared tooth surface must not be below this minimum distance. The minimum distance may vary over the surface of the tooth such that e.g. it is larger near the occlusal surface than near the gingiva. The minimum distance may depend on the choice of material of the dental restoration and aesthetic aspects such as a requested change in the color of the tooth.

The distance may be said to be positive when the virtual validation surface is closer to the center of the tooth than the digital 3D representation. In this case, further preparation of (this part) of the tooth may be needed.

The distance may be said to be negative when the digital 3D representation is closer to the center of the tooth than the virtual validation surface. In this case there is no need for further preparation of (this part) of the tooth.

The distance may be determined at a specific position on the tooth surface. Quite often, the distance varies over the validation surface. The distance may e.g. be positive at some parts of the validation surface and negative at other parts.

In some embodiments, the method for validating the preparation of a tooth comprises determining the distance between the digital 3D representation of the prepared set of teeth and the virtual validation surface or the virtual dental preparation guide during a virtual movement along the insertion direction into the target position of the dental preparation guide.

In some embodiments, the distance is determined as the minimum value (at the specific portion of the validation surface) obtained during the virtual movement along the insertion direction into the target position of the dental preparation guide.

This has the advantage that when preparing the tooth according to the dental preparation guide, it is ensured that the dental restoration can be inserted along the insertion direction onto the prepared to tooth.

In some embodiments, visualizing the virtual dental preparation guide together with the digital 3D representation of the prepared set of teeth comprises using a color coding.

Color coding has the advantage that visual inspection of the current adequateness of the tooth preparation is made easy using e.g. a visual display unit such as a screen.

In some embodiments, the method for validating the preparation of a tooth comprises visualizing the distance at least at some of said one or more selected locations on the tooth surface, such as visualizing the distances using a distance color coding or by indicating the distance using number representing e.g. the distance measured in millimeters.

Different color ranges may be used in the distance color coding, such as a distance color coding where red indicates a positive distance such that the tooth requires further preparation, while blue indicates a negative distance situation, where no further processing is required.

The color coding can be realized by identifying the part of the digital 3D representation of the prepared set of teeth corresponding to the prepared tooth and presenting this part in a different color than the other parts of the digital 3D representation. The other parts may e.g. be visualized in a grey or brownish color while the prepared tooth is visualized in a clear color such as blue or red depending on the distance from the virtual preparation guide surface.

In some embodiments, visualization the virtual dental preparation guide together with the digital 3D representation of the prepared set of teeth comprises a difference map showing differences between the virtual preparation guide surface and shape of the tooth in the digital 3D representation of the pre-prepared or prepared set of teeth. The difference map may visualize the difference using a difference color coding.

The advantage of using such as difference map and difference color coding is that the dentist immediately can see from the visualization which part or parts of the tooth which needs further preparation.

In some embodiments, the method comprises toggling the visualization of the virtual dental preparation guide on and off such that visualizing the virtual preparation guide surface in relation to the digital 3D representation of the prepared teeth comprises changing between visualizing the digital 3D representation of the prepared set of teeth alone and in combination with the virtual preparation guide surface. By toggling the visualization on and off the dentist can easily evaluate which part or parts of the prepared tooth needs further preparation.

In some embodiments, the method comprises toggling the visualization of the virtual dental preparation guide on and off such that visualizing the virtual preparation guide surface in relation to the digital 3D representation of the pre-prepared teeth comprises changing between visualizing the digital 3D representation of the pre-prepared set of teeth alone and in combination with the virtual preparation guide surface. By toggling the visualization on and off the dentist can easily evaluate in which part or parts of the pre-prepared tooth material must be removed in the preparation procedure and how much material he must remove at the different parts of the tooth even before he has started removing any tooth material.

In some embodiments, the method comprises toggling a visualization of a virtual target dental restoration on and off such that a visualization of the virtual target dental restoration in relation to the digital 3D representation of the pre-prepared teeth or the prepared teeth comprises changing between visualizing the digital 3D representation of the pre-prepared teeth or the prepared teeth alone and in combination with the virtual target dental restoration. This provides the dentist with an indication of the how well the virtual target dental restoration is designed for the patient's set of teeth with respect to e.g. the aesthetic appearance of the teeth.

In some embodiments, the visualizing comprises overlaying the virtual preparation guide surface or the virtual dental preparation guide or the virtual validation surface onto the digital 3D representation of the prepared or the pre-prepared set of teeth.

In some embodiments, the visualization comprises visualizing the virtual minimum preparation together with the digital 3D representation of the prepared set of teeth. This provides the dentist with an indication of how far he is from having the tooth prepared according to the virtual minimum preparation and thus how much tooth material must be removed in the different parts of the tooth.

In some embodiments, the virtual dental preparation guide comprises a depth map showing how much tooth material must be removed at the different sections of the tooth in order to provide a shape of the prepared tooth which is acceptable according to the dental preparation guide. The depth map may utilize a depth color coding to visualize how much tooth material must be removed. The advantage of using such a depth map is that it provides the dentist with a direct indication of how much tooth material must be removed in the different parts of the tooth In some embodiments, the method of using the dental preparation guide comprises aligning the virtual dental preparation guide and the digital 3D representation of the prepared set of teeth.

In some embodiments, the virtual validation surface is created according to the shape of the virtual target dental restoration and after being created it is connected with the digital 3D representation of the remaining set of teeth.

In some embodiments, the virtual target dental restoration is connected to the digital 3D representation of the remaining set of teeth and subsequently the virtual validation surface is shaped based on the virtual target dental restoration.

When the virtual dental preparation guide is arranged in a target position relative to a digital 3D representation of the set of teeth, the tooth part of the digital 3D representation of the set of teeth may penetrate into the virtual validation surface if the preparation of the tooth is insufficient. The tooth part of the digital 3D representation may also penetrate into the virtual validation surface during a virtual movement along the insertion direction if the preparation of the tooth is insufficient.

A virtual dental preparation guide can be adjusted during a procedure. The virtual dental preparation guide can be determined from the current shape of the set of teeth in which at least one tooth has been prepared or at least partially prepared. The difference between e.g. the surface of the target restoration and the present shape of the set of teeth defines how much space is provided for the dental restoration. This space can be evaluated such that it can be decided whether there is room for the dental restoration. This evaluation can be made after each drilling of the tooth, and the evaluation may comprise comparing the current shape of the prepared teeth with the virtual validation surface described herein.

In some embodiments, the dental preparation guide is a two-piece device comprising a first and a second part. The first part is formed as a temporary crown and is designed to have an outer surface shaped to resemble a normal tooth surface, and an inner surface with a shape based on the virtual validation surface. The second part is designed to have an inner surface configured for engaging the outer surface of the first part, such that the first and second parts can be releasable connected to form the two-piece dental preparation guide. Since the first and second parts are releasable connected they can be disengaged after the dental preparation guide is used by the dentist for validating the preparation of the tooth. The first part can then be secured at the prepared tooth functioning as a temporary restoration until a final restoration is manufactured.

Disclosed is a two-piece dental preparation guide configured for validating the preparation of at least one tooth for a dental restoration, said dental preparation guide comprising:
 a first formed as a temporary crown, where said first part is designed to have an outer surface shaped to resemble a normal tooth surface and an inner surface with a shape based on the virtual validation surface; and
 a second part designed to have an inner surface configured for engaging the outer surface of the first part, where the second part can be releasable connected with the first part such that the first and the second part together form the dental preparation guide.

After being used by the dentist for validating the preparation of the tooth, the first and second parts of the two-piece dental preparation guide can be disengaged and the first part can be secured at the prepared tooth functioning as a temporary restoration until a final restoration is manufactured. One advantage of this two-piece dental preparation guide is that the portion of the dental preparation guide which is specifically shaped according to the prepared tooth can be reused and that the temporary restoration is readily available when the tooth has been prepared. In prior art methods and dental preparation guides both a dental preparation guide and a temporary crown must be manufactured.

Disclosed is a method for generating a dental preparation guide configured for validating the preparation of at least one tooth in a set of teeth for a dental restoration, said method comprising:

a: virtually forming a remaining set of teeth by virtually removing said at least one tooth from a digital 3D representation of the set of teeth;

b: virtually providing a target dental restoration expressing a target shape of the dental restoration for said at least one tooth, and virtually creating a validation surface based on the target dental restoration; and c: virtually creating the dental preparation guide by combining said validation surface and at least part of the remaining set of teeth.

Disclosed is a method for generating a dental preparation guide configured for validating the preparation of at least one tooth for a dental restoration, said method comprising:

a: obtaining a digital 3D representation of a prepared set of teeth and identifying the portion of the digital 3D representation corresponding to the prepared tooth;

b: generating a virtual minimum restoration surface from the prepared tooth portion and a required minimum thickness of the dental restoration c: determining overlaps between the generated virtual minimum restoration surface and the obtained digital 3D representation of a prepared set of teeth.

Disclosed is a computer program product comprising program code means for causing a data processing system to perform the method according to any of the embodiments, when said program code means are executed on the data processing system.

In some embodiments, the computer program product comprises a computer-readable medium having stored there on the program code means.

Disclosed is a non-transitory computer readable medium storing thereon a computer program, where said computer program is configured for causing computer-assisted generation of dental preparation guide configured for validating the preparation of a tooth for a dental restoration by performing the method according to any of the embodiments.

Disclosed is a system for generating a dental preparation guide configured for validating the preparation of a tooth for a dental restoration, said system comprising:

a scanner configured for obtaining a digital 3D representation of a pre-prepared set of teeth;

means for providing a virtual target dental restoration expressing a target shape of the dental restoration; and means for generating the dental preparation guide from said digital 3D representation of the pre-prepared set of teeth and/or from said virtual target dental restoration, where the dental preparation guide is configured to provide that a preparation of the tooth according to the dental preparation guide will ensure that the dental restoration can be realized and can be inserted at the prepared tooth.

In some embodiments, the means for generating comprises a non-transitory computer readable medium having one or more computer instructions stored thereon, where said computer instructions comprises instructions for performing the method according to the present invention.

Disclosed is a system for generating a dental preparation guide configured for validating the preparation of a tooth for a dental restoration, said system comprising:

a scanner configured for obtaining a digital 3D representation of a pre-prepared set of teeth; and a data processing device configured for generating the dental preparation guide from said digital 3D representation of the pre-prepared set of teeth and/or from a virtual target dental restoration, where the dental preparation guide is configured to provide that a preparation of the tooth according to the dental preparation guide will ensure that the dental restoration can be realized and can be inserted at the prepared tooth, and where said virtual target dental restoration expresses a target shape of the dental restoration;

where the data processing device comprises a non-transitory computer readable medium having one or more computer instructions stored thereon, where said computer instructions comprises instructions for performing the method according to the present invention.

The generated dental preparation guide can be a virtual dental preparation guide, which can be used directly for validating a tooth preparation in a virtual environment and/or which can be used for manufacturing a physical dental preparation guide.

Disclosed is a method for validating a preparation of at least one tooth in a prepared set of teeth for determining whether the prepared tooth is capable of accepting a dental restoration, said method comprising:

obtaining a physical dental preparation guide configured for validating the preparation of the tooth;

arranging the dental preparation guide in relation to the patient's prepared set of teeth;

validating from the physical interaction of the physical dental preparation guide and the prepared set of teeth whether the prepared tooth is shaped such that it can accept the dental restoration.

In some embodiments, the physical dental preparation guide is manufactured from virtual dental preparation guide according to the present invention.

Disclosed is a method for validating a preparation of a tooth in a prepared set of teeth for determining whether the prepared tooth is capable of accepting a dental restoration of a virtual target dental restoration, where said method comprises:

a: obtaining virtual target dental restoration for the set of teeth;

b: obtaining a digital 3D representation of the prepared set of teeth;

c: validating whether the prepared tooth of the prepared set of teeth is shaped such that it can accept the dental restoration.

In some embodiments, the validating comprises visualizing the virtual target dental restoration together with the digital 3D representation of the prepared set of teeth such that the validating can be based on said visualization.

The virtual target dental restoration may comprise a virtual diagnostic wax-up of the set of teeth.

Disclosed is a method for validating the preparation of a tooth for a dental restoration, said method comprising:

obtaining a virtual dental preparation guide configured for validating the preparation of the tooth;

obtaining a digital 3D representation of the prepared set of teeth; and visualizing the virtual dental preparation guide together with the digital 3D representation of the prepared set of teeth Disclosed is a user interface for generating a dental preparation guide configured for validating the preparation of at least one tooth for a dental restoration, where the user interface is configured for:

a: obtaining a digital 3D representation of a pre-prepared set of teeth;

b: virtually removing said at least one tooth from the digital 3D representation of the pre-prepared set of teeth, such that a digital 3D representation of a remaining set of teeth is formed;

c: providing a virtual target dental restoration expressing a target shape of the dental restoration;

d: creating a virtual validation surface for the dental preparation guide based on the virtual target dental restoration, where the validation surface is such that the preparation of the tooth can be validated by the dental preparation guide; and e: creating a virtual preparation guide surface by combining the virtual validation surface and at least part of the surface of the digital 3D representation of the remaining set of teeth.

Disclosed is a user interface for generating a dental preparation guide configured for validating the preparation of at least one tooth for a dental restoration, where the user interface is configured for:

virtually removing said at least one tooth from an obtained digital 3D representation of the pre-prepared set of teeth, such that a digital 3D representation of a remaining set of teeth is formed;

creating a virtual validation surface for the dental preparation guide based on a provided virtual target dental restoration expressing a target shape of the dental restoration, where the validation surface is such that the preparation of the tooth can be validated by the dental preparation guide; and creating a virtual preparation guide surface by combining the virtual validation surface and at least part of the surface of the digital 3D representation of the remaining set of teeth.

In some embodiments, the user interface is configured for visualizing the obtained digital 3D representation of a pre-prepared set of teeth and the created virtual preparation guide surface.

The visualization can be performed sequentially such that at least one of the visualized items is visualized before at least one of the other visualized items. A number of the visualized items can also be visualized simultaneously, such as in cases where the created virtual validation surface and the digital 3D representation of the remaining teeth are visualized in one part of the user interface, and the digital 3D representation of the pre-prepared set of teeth is visualized in another part.

In some embodiments, the user interface is configured for being visualized to an operator using a computer screen and for allowing the operator to enter data into and make choices presented in the user interface by means of a computer keyboard or a computer mouse.

In some embodiments, the user interface is configured for visualizing the virtual preparation guide surface together with the digital 3D representation of the prepared set of teeth, and the user interface comprises a virtual toggling tool for toggling between visualizing the digital 3D representation of the prepared set of teeth alone and in combination with the virtual preparation guide surface when activated.

In some embodiments, the user interface is configured for visualizing the virtual preparation guide surface together with the digital 3D representation of the pre-prepared set of teeth, and the user interface comprises a virtual toggling tool for toggling between visualizing the digital 3D representation of the pre-prepared set of teeth alone and in combination with the virtual preparation guide surface when activated.

The user interface can be implemented using a computer system where the user interface is visualized using a computer screen showing the different components of the user interface, such a data entry fields and virtual push buttons configured for performing one or more steps of a method according to an embodiment of the invention. Data entry means such as a computer mouse and a computer keyboard can be connected to the computer system and used for entering data into the user interface and for making selections by e.g. pressing said virtual push buttons using the computer mouse.

In some embodiments, the user interface is configured for allowing an operator to carry out a method according to an embodiment of the invention. Preferably, at least one of the steps of obtaining a digital 3D representation of a pre-prepared set of teeth and forming a digital 3D representation of a remaining set of teeth by virtually removing said at least one tooth from the digital 3D representation of the pre-prepared set of teeth, providing a virtual target dental restoration expressing a target shape of the dental restoration, creating a virtual validation surface for the dental preparation guide based on the virtual target dental restoration, and creating a virtual preparation guide surface by combining the virtual validation surface and at least part of the surface of the digital 3D representation of the remaining set of teeth can be performed by the operator using said user interface. In some embodiments, the steps of the method are performed sequentially and the user interface can be configured for sequentially providing a visually representation of the steps to the operator such that the sequence of the user interface matches that of the method. In some embodiments, the user interface is configured for simultaneously providing a visually representation of two or more of the steps to the operator.

The present invention relates to different aspects including the methods, uses and systems described above and in the following, and corresponding methods, uses and systems, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 11A through 11D show an example of an embodiment of the invention for forming a virtual preparation guide surface.

In the following description, reference is made to the accompanying figures, which show by way of illustration how the invention may be practiced.

Figure 1:
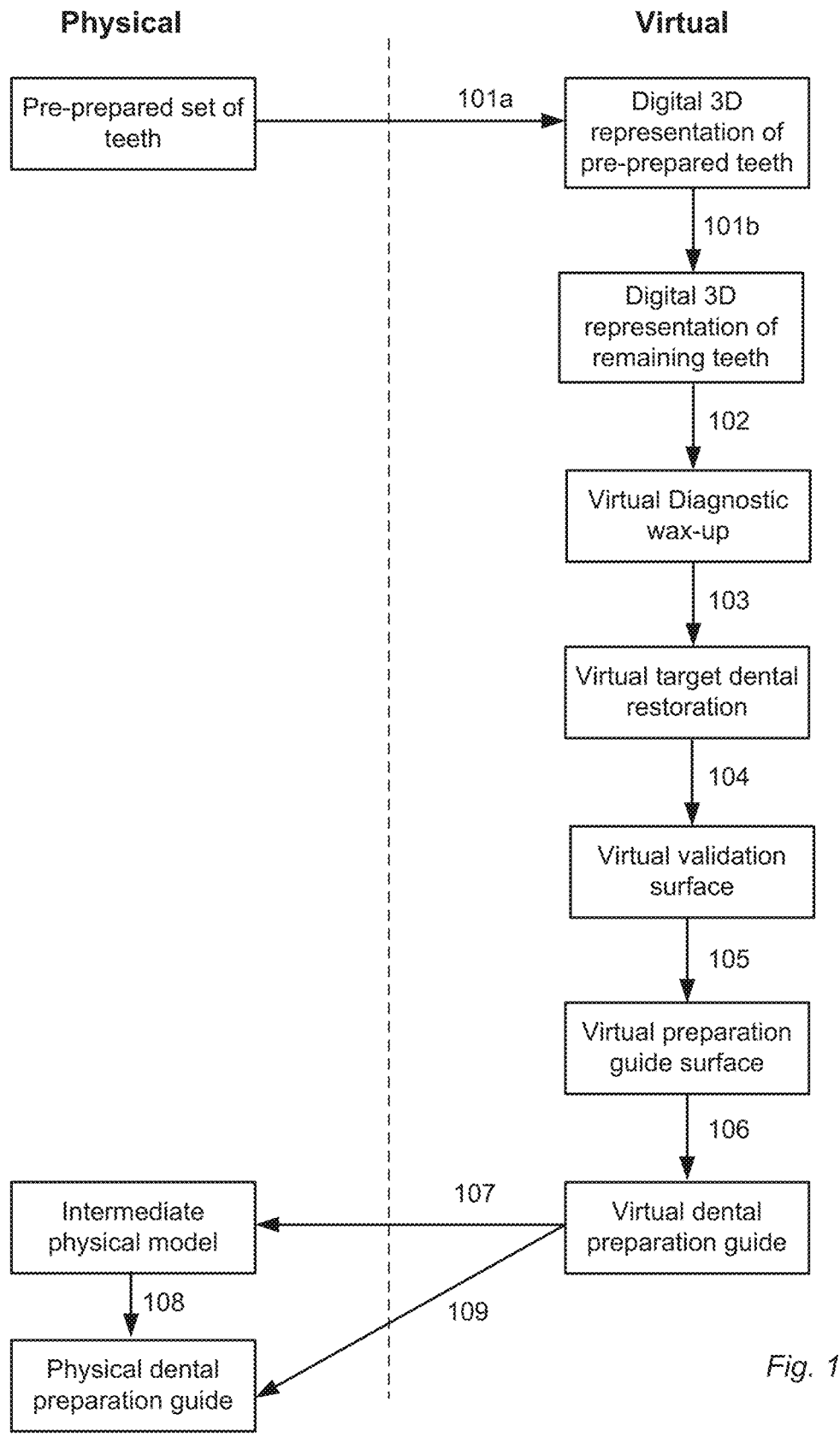
FIG. 1 shows a flowchart for an embodiment of the method for generating a dental preparation guide.
Figure 2:
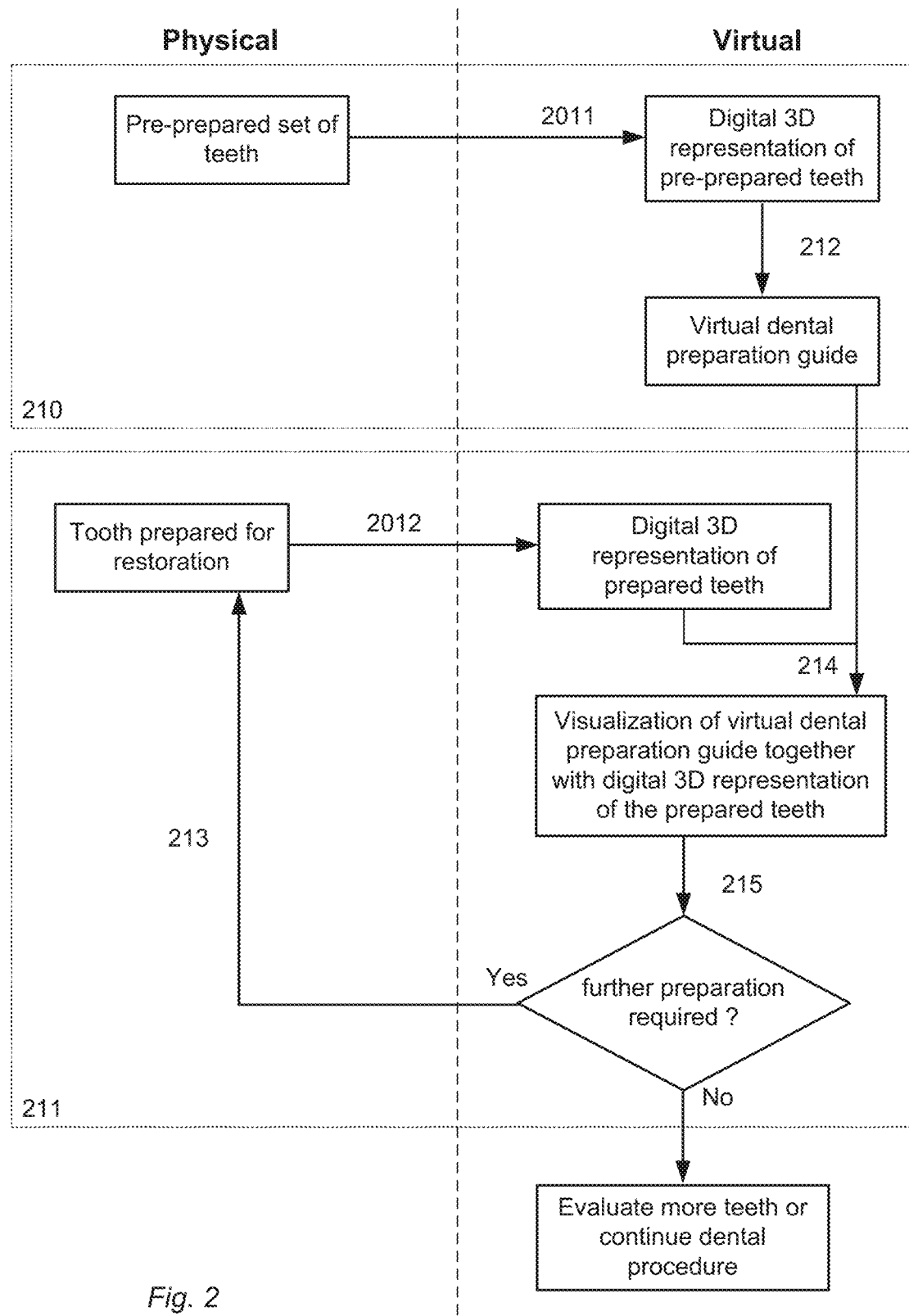
FIG. 2 shows an example of a flowchart for generating a virtual dental preparation guide and for using it to validate a tooth preparation.
Figure 14:
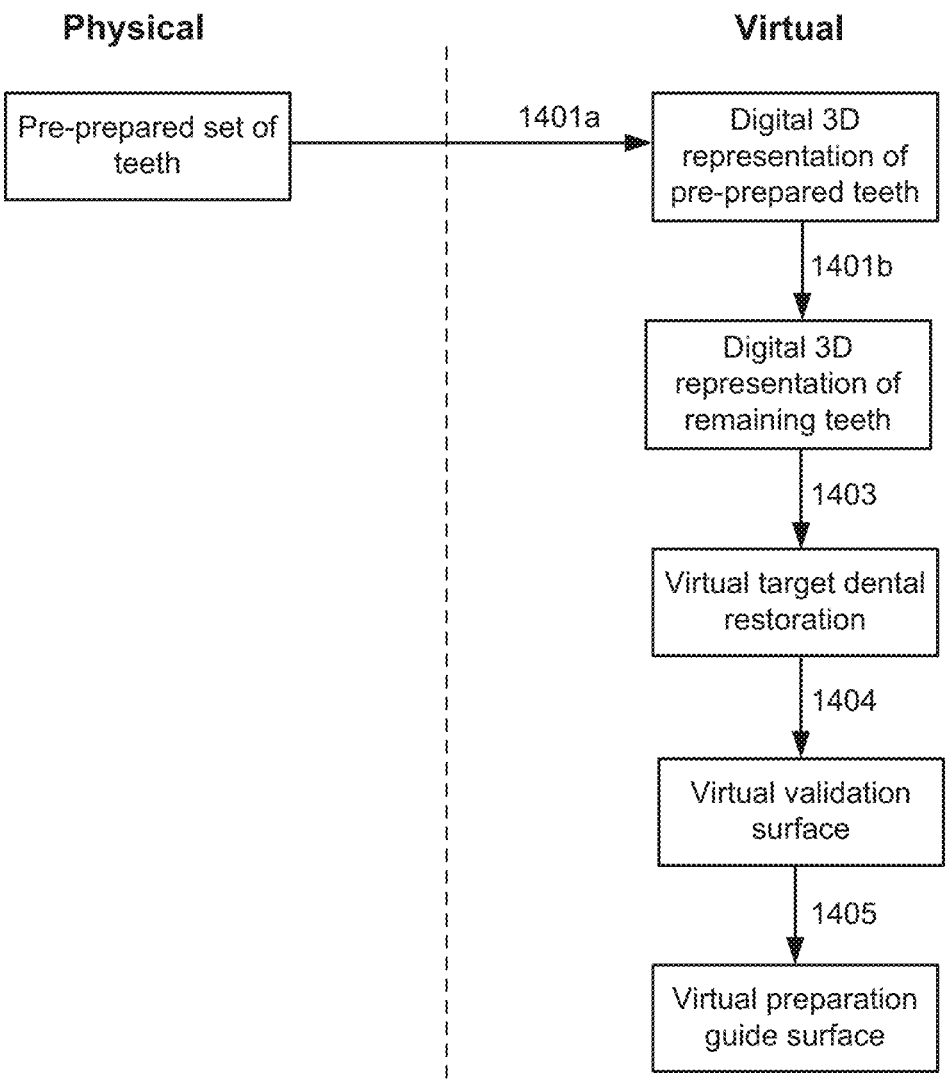
FIG. 14 shows a flowchart for an embodiment of the method for generating a dental preparation guide.

In the flow-charts of FIGS. 1, 2 and 14, the vertical dotted line at the center divides the work-flows into a part relating to physical units (left-hand side) and a part relating to virtual units (right-hand side) in the workflow.

FIG. 14 shows a flowchart 1400 for an embodiment of the method for generating a dental preparation guide for validating the preparation of a tooth for a dental restoration.

In step 1401a, a digital 3D representation of the pre-prepared set of teeth is obtained, e.g. by direct intra-oral scanning of the set of teeth or by scanning a physical model or an impression of the pre-prepared set of teeth.

In step 1401b, the portion of this digital 3D representation corresponding to the tooth or teeth which the dental preparation guide is generated for is virtually removed such that a digital 3D representation of a remaining set of teeth is formed.

In step 1403, a virtual target dental restoration is created. The virtual target dental restoration can be created based on a virtual diagnostic wax-up for the set of teeth where the virtual diagnostic wax-up expresses a target shape of the virtual target dental restoration.

In step 1404 the virtual validation surface is created based in the virtual target dental restoration and in step 1405 the virtual preparation guide surface is created by connecting the virtual validation surface and the surface of the digital 3D representation of the remaining set of teeth.

FIG. 1 shows a flowchart 100 for an embodiment of the method for generating a physical dental preparation guide for validating the preparation of a tooth.

In step 101a a digital 3D representation of the pre-prepared set of teeth is obtained, e.g. by direct intra-oral scanning of the set of teeth or by scanning a physical model or an impression of the pre-prepared set of teeth.

In step 101b, the portion of this digital 3D representation corresponding to the tooth or teeth which the dental preparation guide is generated for is virtually removed such that a digital 3D representation of a remaining set of teeth is formed.

In step 102 a virtual diagnostic wax-up for the set of teeth is designed such that it expresses a target shape of the dental restoration. The virtual diagnostic wax-up is based on one or more aesthetic parameters which can relate to the shape of the individual teeth, the color of the teeth, and/or the relative arrangement of the teeth. The material of the dental restoration can be decided based on e.g. patient's choice or practical dental concerns, such as size and form of tooth or teeth that are to be restored. There must further be enough space for the dentist to perform the necessary steps in the preparation of the tooth and for inserting the dental restoration at the prepared tooth. The minimum thickness of the restoration material also depends on the desired change of color. A large change may require a larger thickness.

The virtual target dental restoration is created based on the designed virtual diagnostic wax-up in step 103, and in step 104 the virtual validation surface is created based in the virtual target dental restoration.

In step 105 the virtual preparation guide surface is created by connecting the virtual validation surface and the surface of the digital 3D representation of the remaining set of teeth.

In step 106, at least a selected part of the virtual preparation guide surface is shelled such that the virtual dental preparation guide comprises an inner shell surface and an outer shell surface in the selected part.

In some cases the outer shell surface is shaped according to the created virtual preparation guide surface and the shelling can be used to define the inner shelling surface from the outer surface, i.e. from the virtual preparation guide surface. In such cases, an intermediate physical model can be manufactured from the shelled virtual preparation guide surface in step 107 using direct digital manufacturing. The physical dental preparation guide is then manufactured in step 108 by shaping the material of the dental preparation guide using said intermediate physical model. The material of the dental preparation guide can be shaped by vacuum forming it onto the intermediate physical model.

In some cases the inner shell surface is shaped according to the virtual preparation guide surface and the shelling can be used to define the outer shell surface from the inner shell surface, i.e. from the virtual preparation guide surface. In such cases, the physical dental preparation guide is manufactured in step 109 from the shelled virtual preparation guide surface using e.g. 3D printing.

FIG. 2 shows an example of a flowchart for generating a virtual dental preparation guide and for using it to validate a tooth preparation. The flowchart contains a part 210 concerning the generation of the virtual dental preparation guide and a part 211 for using the generated virtual dental preparation guide to validate the preparation of the tooth.

In step 2011, a digital 3D representation of the pre-prepared set of teeth is obtained by direct intra-oral scanning of the teeth. A virtual dental preparation guide is then created in step 212 using e.g. steps 102 to 106 of the workflow described in relation to FIG. 1 or steps 1401a to 1404 described in relation to FIG. 14.

The tooth or teeth are prepared for the restoration by grinding away tooth material. The patient's set of teeth is then referred to as a prepared set of teeth.

In step 2012 the intra-oral scanner is used to scan at least the region of the prepared set of teeth in which the prepared tooth or teeth are located in order to obtain a digital 3D representation of the prepared set of teeth.

In step 214 the digital 3D representation of the prepared set of teeth and the virtual dental preparation guide are aligned and visualized together on a visual display unit, such as on a computer screen.

Based on the aligned digital 3D representation of the prepared set of teeth and virtual dental preparation guide a validation of the tooth preparation is performed in step 215 to determine whether further preparation is required.

If further preparation is required, the dentist continues the preparation in step 213. A new intra-oral scanning 2012, alignment 214 and validation 215 is then performed and the loop continues until no further preparation of the tooth is required and the dentist chooses to proceed to a following part of the dental procedure.

The intra-oral scanner may be configured for utilizing focus scanning, where the digital 3D representation of the scanned teeth is reconstructed from in-focus images acquired at different focus depths. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor comprises an array of sensor elements. The position of the focus plane relative to the set of teeth is varied by means of focusing optics while images are obtained from said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the light oscillation amplitude for each of a plurality of the sensor elements or each of a plurality of groups of the sensor elements for a range of focus planes. From the in-focus positions, the digital 3D representation of the set of teeth can be derived.

Creating the dental preparation guide and the use of it may run in parallel with the preparation of the tooth or teeth, and may as such not be part of a treatment on the patient but rather be a method for generating and for using a guide for validating the preparation of the teeth.

In the text above the method is described in relation to the evaluation of one tooth preparation. The method is evidently also suited for simultaneously evaluating the preparation of a number of teeth.

Figure 3A:
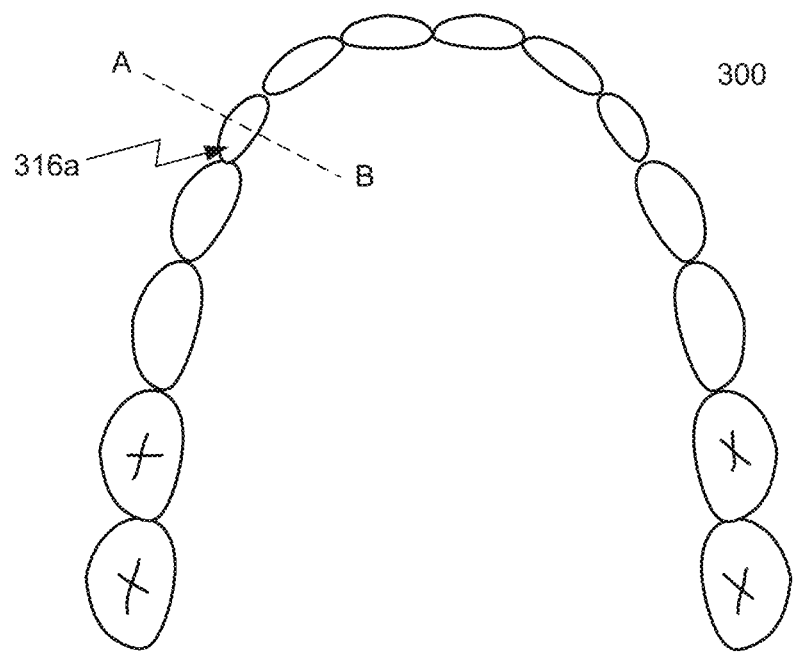
FIGS. 3A and 3B show a schematic of teeth in one jaw of a patient and cross sectional presentations relating to some of the surfaces involved in generating the virtual preparation guide surface.

FIG. 3a shows a schematic of teeth in one jaw of a patient and a cross sectional plane at a tooth which is to be prepared.

The set of teeth 300 has a tooth 316a which e.g. is ill and in need of a dental restoration such as a crown. The tooth must hence be prepared such that it is capable of accepting the crown. The plane in which the cross sectional view is obtained is defined by the line A-B crossing the tooth and the normal to the occlusal plane of the set of teeth, i.e. the plane is perpendicular to the occlusal plane.

FIGS. 3b to 9, 11, and 15 to 17 show cross sectional representations of the teeth and the dental preparation guide as seen in the plane defined in FIG. 3a.

Figure 3B:
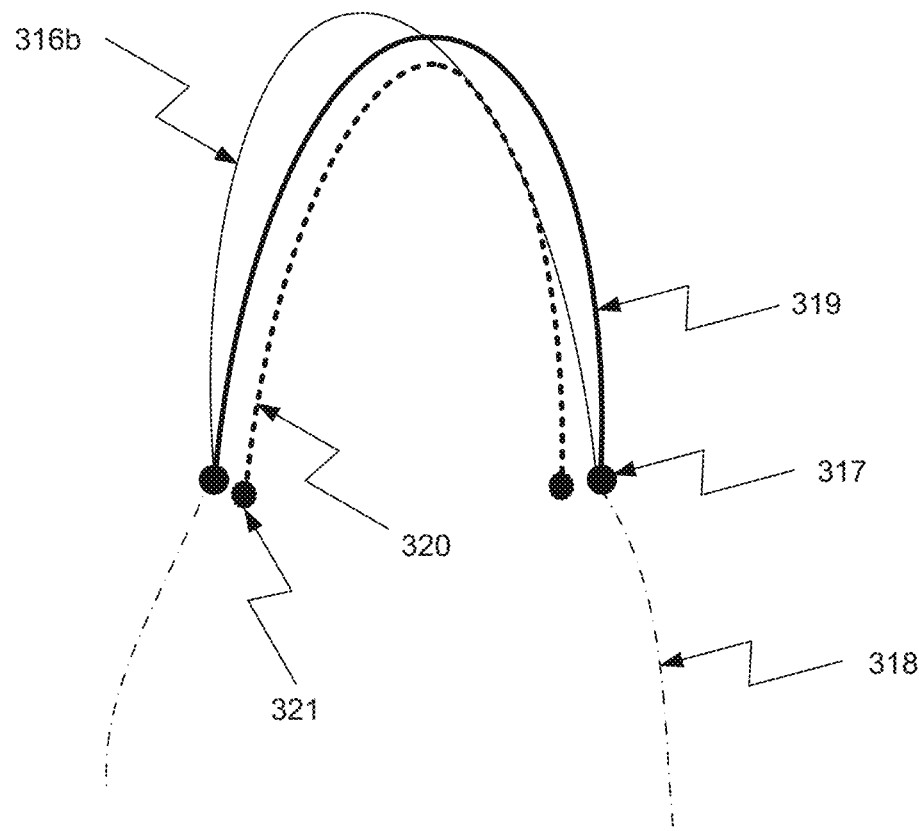

FIG. 3b shows cross sectional presentations relating to some of the surfaces involved in generating the virtual preparation guide surface.

The tooth portion 316b of digital 3D representation of the pre-prepared set of teeth is virtually removed at a boundary determined by the 3D sectioning spline 317. When the tooth is virtually removed a virtual hole is introduced in the digital 3D representation of the remaining set of teeth 318.

In this example, the virtual target dental restoration is based on a virtual diagnostic wax-up 319 designed according e.g. to the patient's aesthetic preferences.

The virtual validation surface 320 is based on a virtual minimum preparation surface defined by inward offsetting the virtual diagnostic wax-up 319 and by pushing a portion of the offset surface which extends beyond the tooth portion 316b onto the tooth portion to provide that the virtual validation surface follows the tooth surface at this part of the tooth. A virtual preparation line 321 is also illustrated in the figure.

With the virtual validation surface 320 described by the minimum preparation surface, the virtual preparation guide surface can be created by connecting the digital 3D representation of the remaining set of teeth 318 and the virtual minimum preparation surface.

Figure 4:
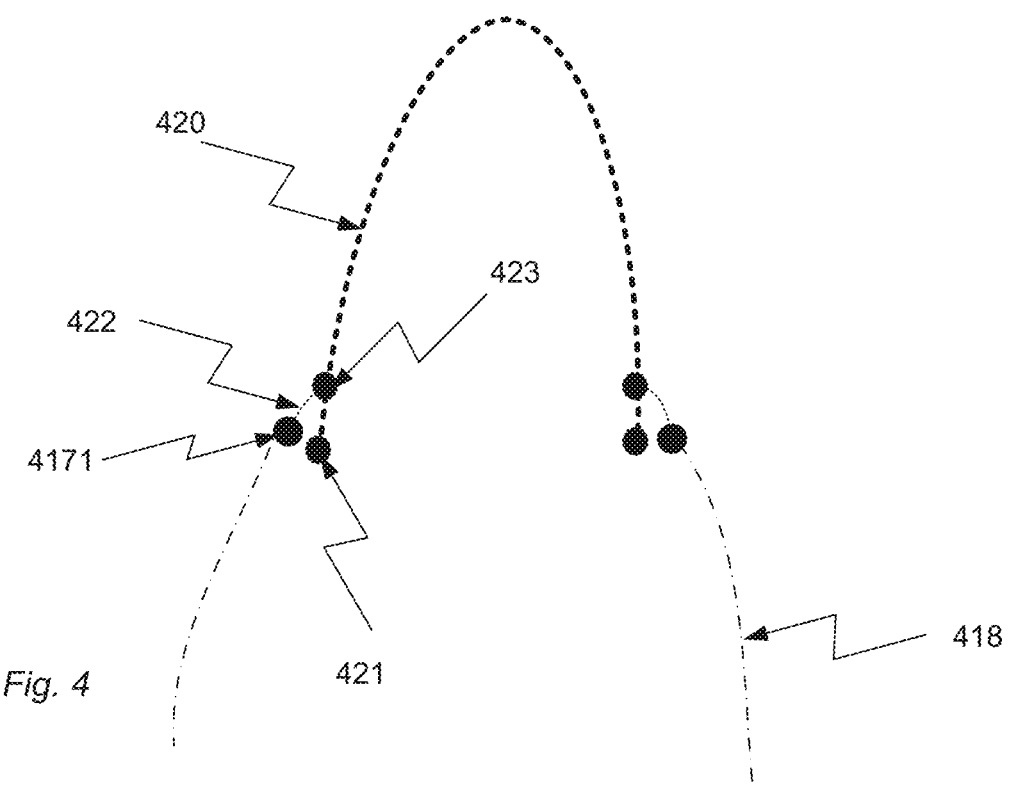
FIG. 4 shows an example on how a digital 3D representation of the remaining set of teeth and a virtual validation surface can be connected.

FIG. 4 shows an example on how a digital 3D representation of the remaining set of teeth and a virtual validation surface can be connected.

A 3D remaining teeth spline 4171 has been determined based on the 3D sectioning spline seen in FIG. 3. Since the virtual validation surface 420 which is based on the virtual minimum preparation surface is smaller than the corresponding part of the digital 3D representation of the pre-prepared set of teeth, there is a hole between the virtual validation surface 420 and the digital 3D representation of the remaining set of teeth 418.

The virtual preparation guide surface is created by connecting the virtual validation surface 420 and the digital 3D representation of the remaining set of teeth 418. These surfaces are connected by creating a connecting surface 422 extending from the 3D remaining teeth spline 4171 to a 3D validation surface spline 423. Here the 3D validation surface spline 423 is arranged above the virtual preparation line 421, but it can in principle be arranged at any location on the virtual validation surface, such as substantially along the virtual preparation line 421.

The connecting surface 422 can be created in a lofting process.

The 3D remaining teeth spline 4171 can be determined by modifying the 3D sectioning spline which was defined in relation to the digital 3D representation of the pre-prepared set of teeth. In some embodiments, the modification is aided by visualizing the 3D sectioning spline in relation to the surface of a virtually removed tooth or a tooth of the virtual target dental restoration. When visualized in relation to a virtually removed tooth, any interproximal holes on the virtually removed tooth may have been closed previously using e.g. curvature-based algorithms.

In order to provide a watertight virtual preparation guide surface, further hole-closing may be needed. This may be performed using curvature based hole-closing algorithms.

Figure 5:
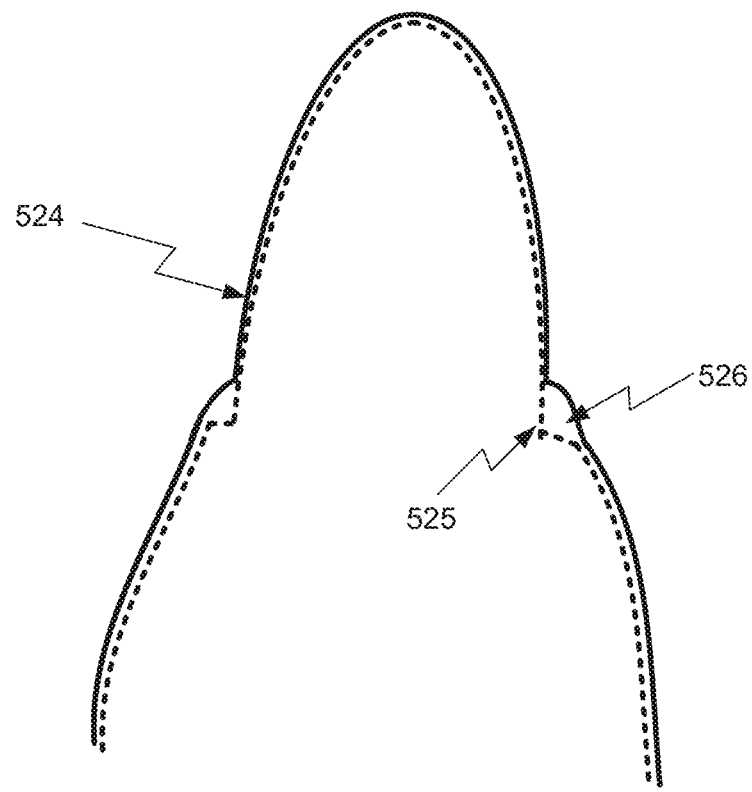
FIG. 5 shows an example of a virtual preparation guide surface

FIG. 5 shows an example of a virtual preparation guide surface.

The virtual preparation guide surface 524 illustrated in this figure is created from the virtual validation surface, the connecting surface, and the digital 3D representation of the remaining set of teeth as seen in FIG. 4. The virtual preparation guide surface 524 is here aligned with a digital 3D representation of the prepared set of teeth 525.

Due to the location of the 3D validation surface spline above the virtual preparation line in FIG. 4, a safety zone 526 is provided at the preparation line allowing the dentist some room for maneuvering, such as to adjust the actual position of the preparation line during the dental procedure.

Figure 6:
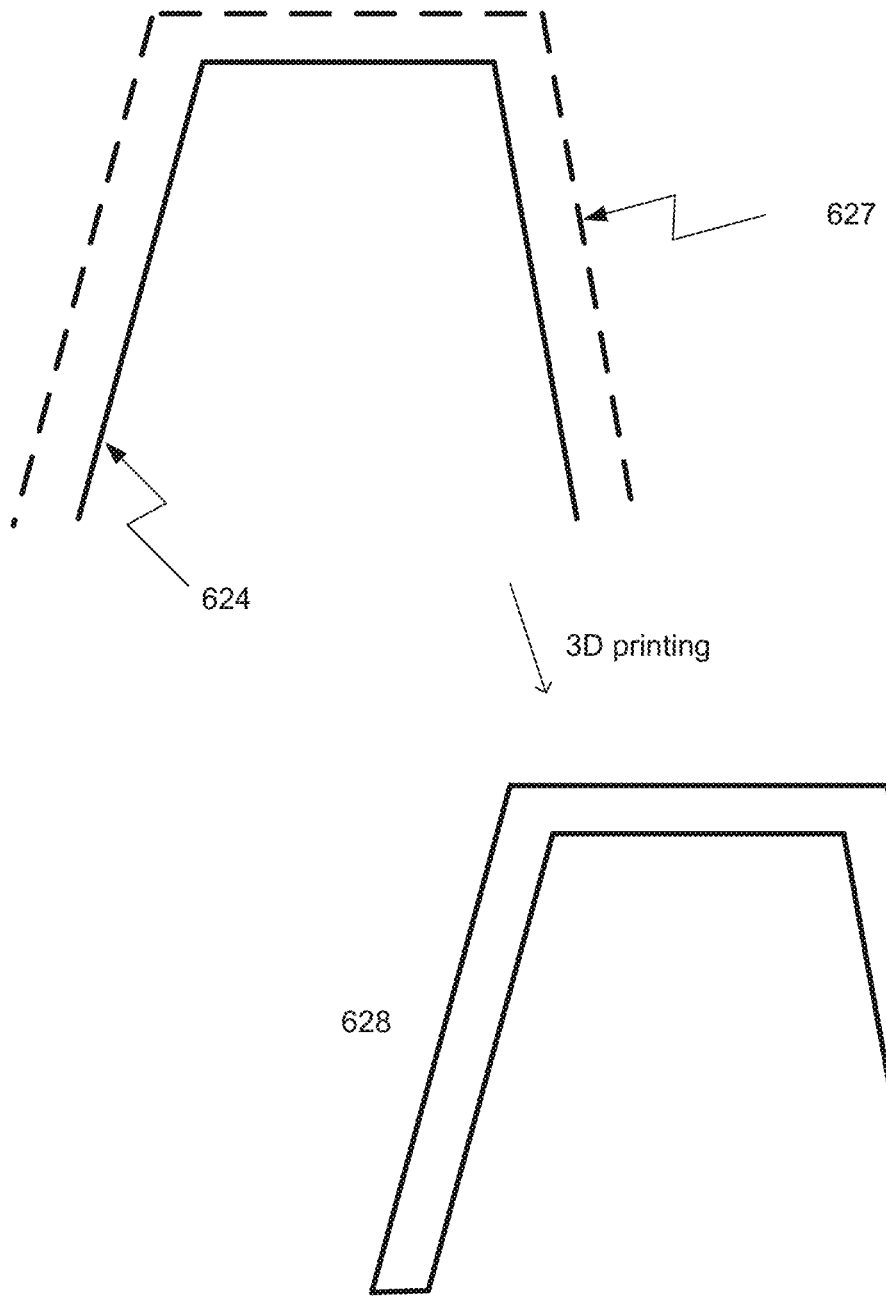
FIG. 6 shows a path for manufacturing the dental preparation guide from the virtual preparation guide surface.

FIG. 6 shows one path for manufacturing the dental preparation guide from the virtual preparation guide surface. In this embodiment, the physical dental preparation guide is manufactured directly from the virtual dental preparation guide.

The virtual preparation guide surface 624 representing an inner shell surface is offset outward to provide an outer shell surface 627. Based on the shelled virtual preparation guide surface, a physical dental preparation guide 628 can be manufactured using direct digital manufacturing such as 3D printing. The surface of the dental preparation guide facing the set of teeth is shaped according to the virtual preparation guide surface.

In the context of the present invention, the phrase "surface is offset outward" corresponds to offsetting the surface away from the position where the teeth are located when the dental preparation guide is arranged in relation to the patient's teeth.

Figure 7:
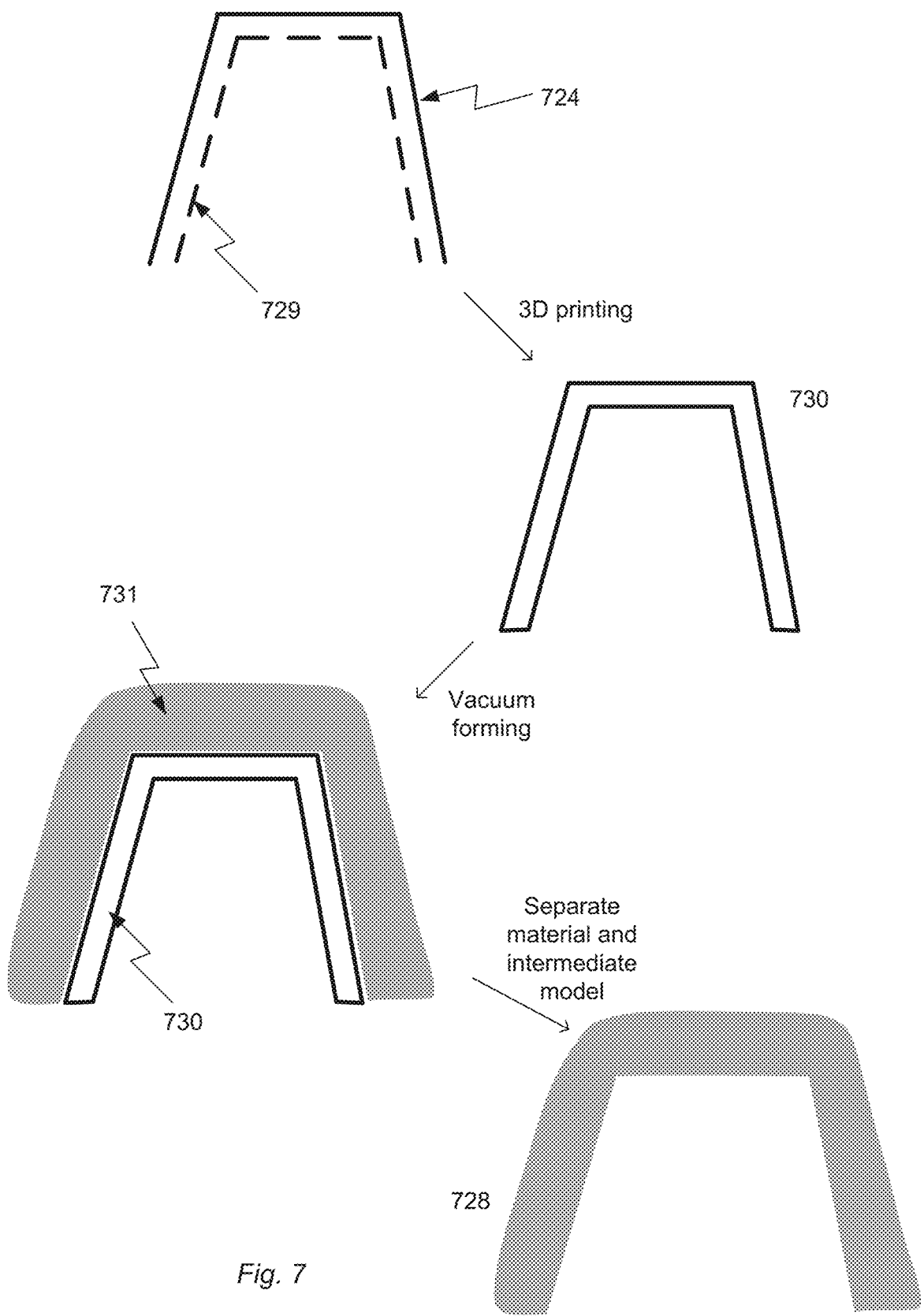
FIG. 7 shows a path for manufacturing the dental preparation guide from the virtual preparation guide surface.

FIG. 7 shows one path for manufacturing the dental preparation guide from the virtual preparation guide surface. In this embodiment, the physical dental preparation guide is manufactured via an intermediate physical model formed based on the virtual dental preparation guide.

The virtual preparation guide surface 724 representing an outer shell surface is offset inward to provide an inner shell surface 729. Based on the shelled virtual preparation guide surface, an intermediate physical model 730 can be manufactured using direct digital manufacturing, such as 3D printing. In the context of the present invention, the phrase "surface is offset inward" corresponds to offsetting the surface towards the position where the teeth are located when the dental preparation guide is arranged in relation to the patient's teeth.

Dental preparation guide material 731 is then shaped according to the intermediate physical model 730 by e.g. vacuum forming the material 731 onto the intermediate physical model 730. The dental preparation guide material 731 is then separated from the intermediate model 730 to provide the physical dental preparation guide 728, where the surface facing the set of teeth is shaped according to the virtual preparation guide surface.

Figure 8:
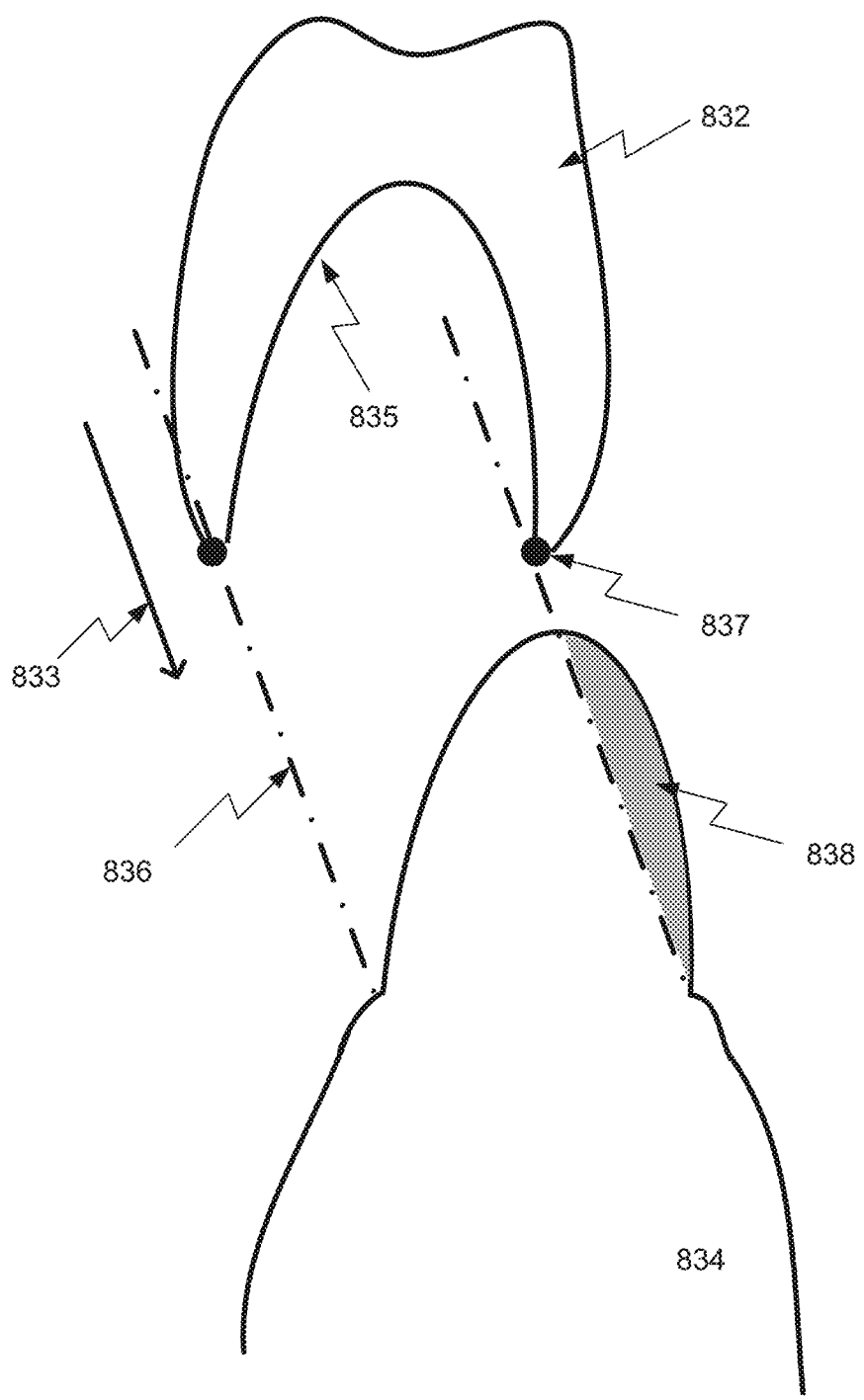
FIG. 8 shows a situation where the insertion direction preferably should be taken into account.

FIG. 8 shows a situation where the insertion direction preferably should be taken into account in order to generate a dental preparation guide which also takes into account that the dental restoration moves along a path when being arranged in relation to the patient's set of teeth.

A dental restoration 832 is moved along a path determined by the insertion direction 833 towards its target position relative to the prepared set of teeth 834. The inner surface 835 of the dental restoration 832 matches the corresponding portion of the prepared set of teeth.

The lines 836 indicate the trace of a margin line 837 of the dental restoration when the dental restoration is moved along the path determined by the insertion direction 833. One of these lines cut through the prepared set of teeth 834 showing that a collision between the prepared set of teeth 834 and the cervical part of the dental restoration will prevent the dental restoration 832 from being arranged in the target position unless the region 838 is removed. That is the virtual preparation guide surface may be shaped to ensure that if the tooth is prepared according to the virtual preparation guide surface, the dental restoration 832 can be moved into the target position without any collisions.

FIG. 9 shows how the insertion direction can be taken into account when designing the dental preparation guide. Instead of using an approach where the dental restoration is trimmed to compensate for the insertion direction, the dental preparation guide is trimmed.

Figure 9A:
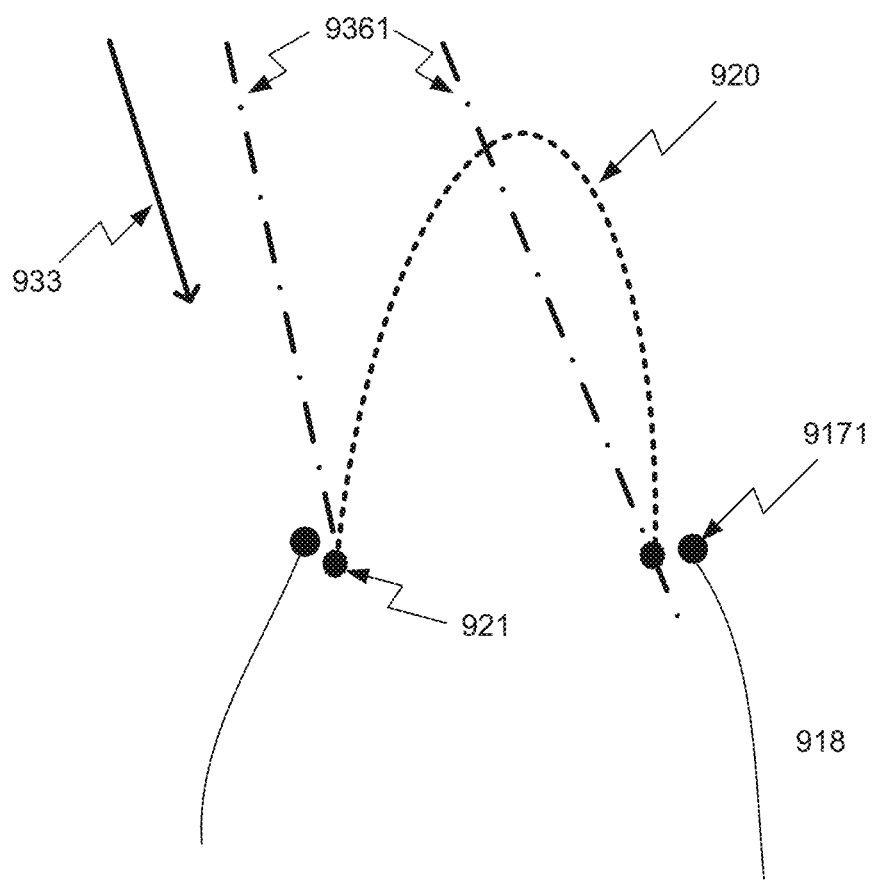
FIGS. 9A through 9C show how the insertion direction can be taken into account when designing the dental preparation guide.

FIG. 9a shows the virtual validation surface 920 which is intersected by one of the paths 9361 which are arranged to pass through the virtual preparation line 921. Here the paths 9361 are arranged at an angle of 5 degrees relative to the insertion direction 933 to provide that the prepared tooth is tapered. In the illustrated situation, the taper is only strictly necessary on the path cutting through the virtual validation surface 920.

Figure 9B:
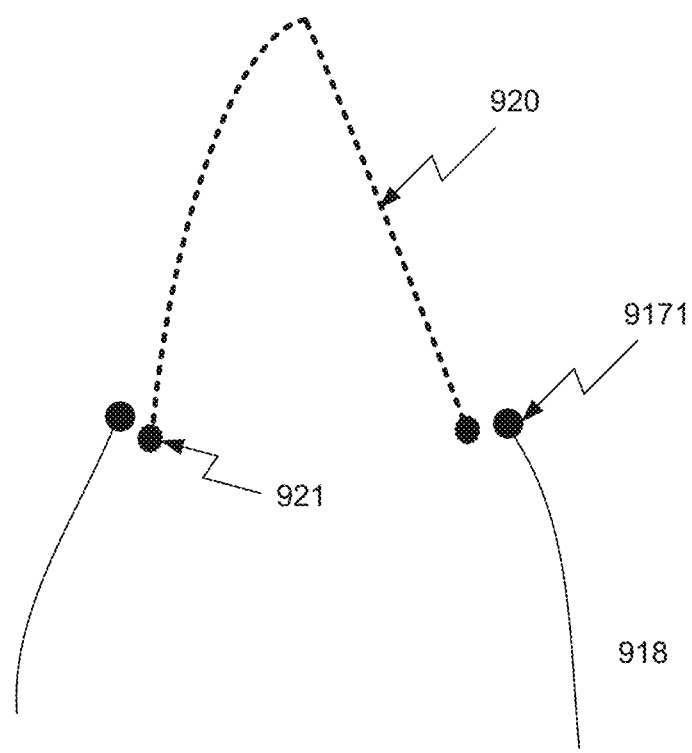

In order to take into account the insertion direction 933 (and in this example also the taper angle) the virtual validation surface 920 is trimmed such that the surface of the intersected part is aligned with the path intersecting it, thereby removing the region blocking the path of the cervical part of the dental restoration. The trimmed virtual validation surface 920 is seen in FIG. 9b.

The trimmed virtual validation surface 920 can then be connected to the digital 3D representation of the remaining set of teeth 918 at the 3D remaining teeth spline 9171 to provide the virtual preparation guide surface using e.g. lofting as described above.

Figure 9C:
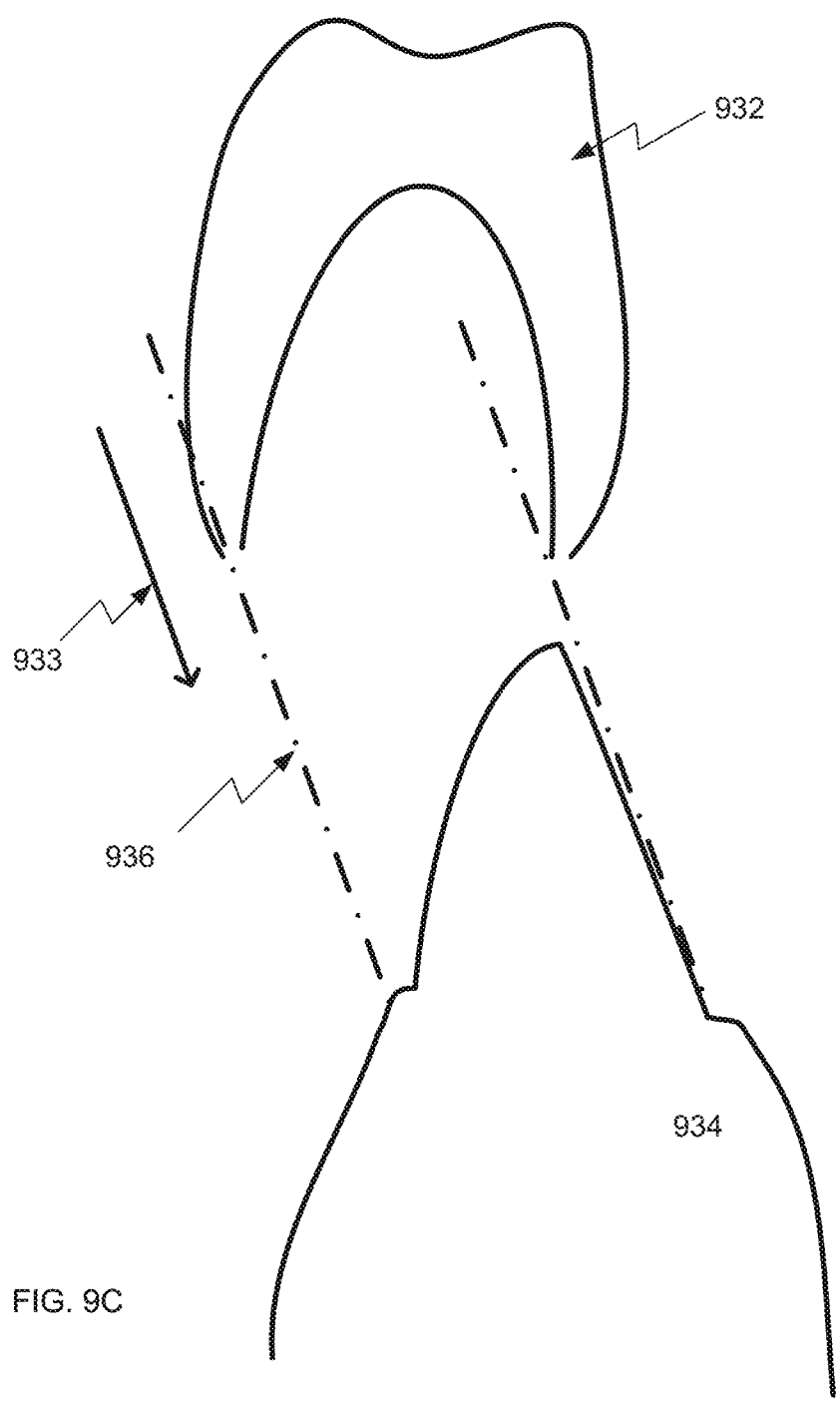

FIG. 9c then shows the situation after the insertion direction has been taken into account when designing the virtual validation surface and hence the virtual preparation guide surface.

Now the dental restoration 932 can moved along the path 936 determined by the insertion direction 933 towards its target position relative to the prepared set of teeth 934 without being blocked by tooth material.

A slight angle is seen between the path 936 and the portion of the prepared set of teeth 934 corresponding to the trimmed portion of the virtual validation surface. This is caused by the taper angle.

Figure 10A:
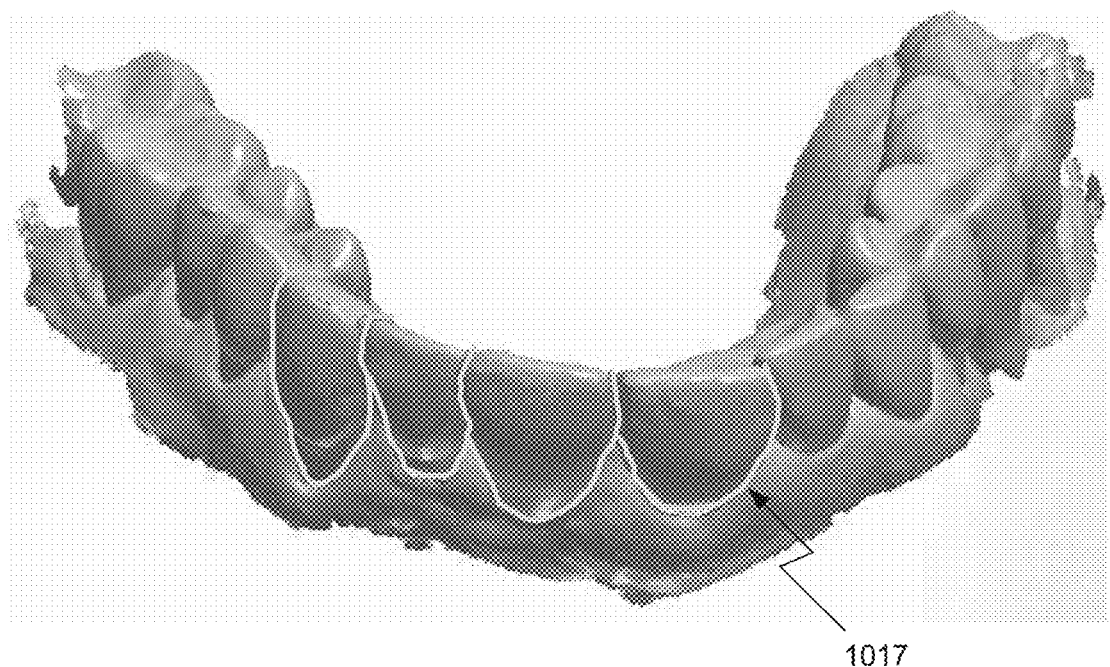
FIGS. 10A and 10B show screen shots in which the virtual removal of teeth introduces virtual holes in the digital 3D representation of the remaining teeth.
Figure 10B:
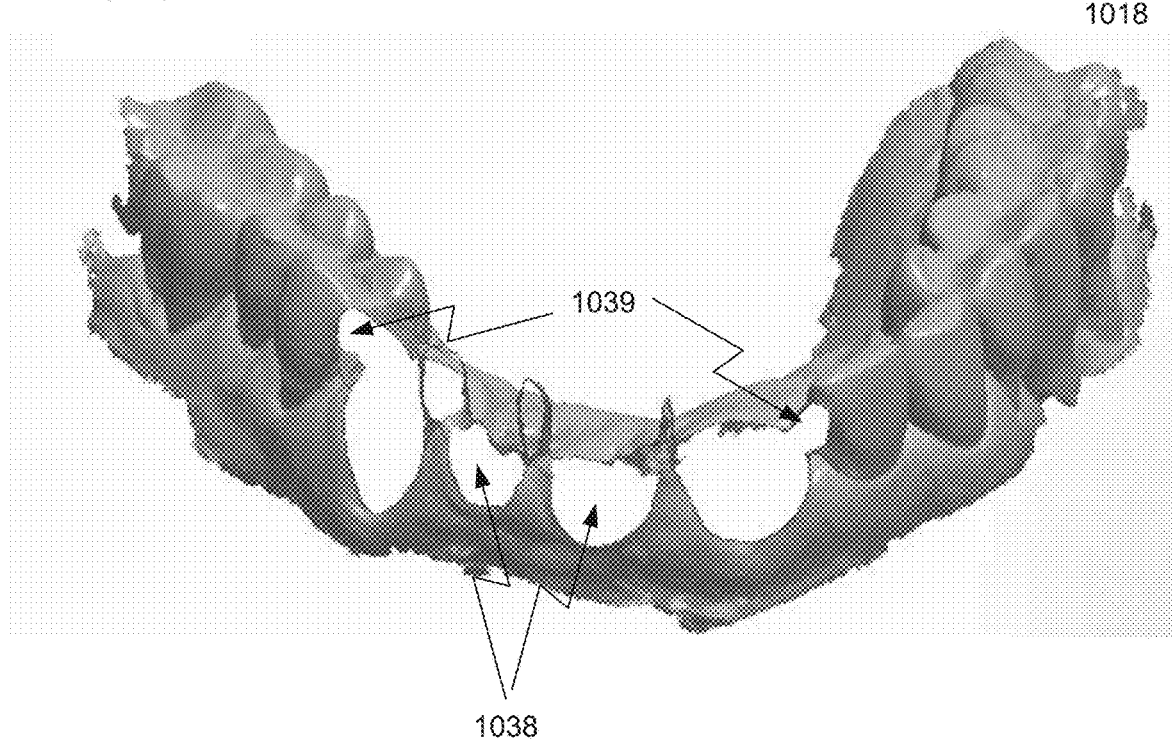

FIG. 10 shows screen shots in which the virtual removal of teeth introduces virtual holes in the digital 3D representation of the remaining teeth 3D sectioning splines 1017 are defined in relation to the digital 3D representation of the pre-prepared set of teeth 1037 such that 4 teeth can be virtually removed. The 3D sectioning splines 1017 may be defined automatically by e.g. extracting boundaries of the teeth portion of the digital 3D representation of the pre-prepared set of teeth.

When the teeth are virtually removed, virtual holes appear in the digital 3D representation of the remaining set of teeth 1018. The virtual holes include four virtual gingival holes 1038, and interproximal holes 1039 at the portions of the digital 3D representation of the remaining set of teeth corresponding to the neighboring teeth. Here no boundary exist between each interproximal hole is and the neighboring gingival hole.

A virtual hole can be closed by a virtual replacement surface or be closed by virtual gingival and virtual interproximal surfaces.

When a virtual hole is closed using a virtual replacement surface, the interproximal sections of the 3D remaining teeth spline can be defined in relation to this virtual replacement surface. The 3D remaining teeth spline may be arranged to divide a portion of the virtual replacement surface into a virtual gingival surface and a virtual interproximal surface.

FIG. 11 shows how a virtual preparation guide surface with a virtual validation surface according to a diagnostic wax-up can be created.

In FIG. 11a, a virtual hole in the digital 3D representation of the remaining set of teeth 1118 is bounded by a 3D remaining teeth spline 11171. The 3D remaining teeth spline can be determined from a 3D sectioning spline such as the 3D sectioning spline 1017 illustrated in FIG. 10.

In FIG. 11b, a virtual replacement surface 1140 is connected to the digital 3D representation of the remaining set of teeth 1118 at the 3D remaining teeth spline 11171 such that the virtual hole in the digital 3D representation of the remaining set of teeth 1118 is closed.

In FIG. 11c, a virtual target dental restoration 1141 defined from a virtual diagnostic wax-up is aligned with the digital 3D representation of the remaining set of teeth 1118 such that it is intersected by the portion corresponding to the virtual replacement surface. The virtual validation surface can here be considered to be the portion of the virtual target dental restoration 1141 arranged above the digital 3D representation of the remaining set of teeth 1118.

The virtual preparation guide surface 1124 can then be created by a Boolean addition of the virtual target dental restoration 1141 and the digital 3D representation of the remaining set of teeth 1118. The resulting virtual preparation guide surface 1124 is seen in FIG. 11d.

Alternatively to connecting a virtual replacement surface to the digital 3D representation of the remaining set of teeth, the interproximal hole may at least partly be closed by a virtual interproximal surface while the gingival hole may be closed by a virtual tooth preparation or by a virtual gingival depending on whether a crown or a pontic is to be arranged at the location of the gingival hole. The virtual preparation guide surface may then be created by a Boolean addition of the digital 3D representation of the remaining set of teeth and the virtual tooth preparation or the virtual gingival. The boundary between the virtual interproximal surface and the virtual gingival or the virtual tooth preparation can be used for defining the 3D remaining teeth spline.

Figure 12:
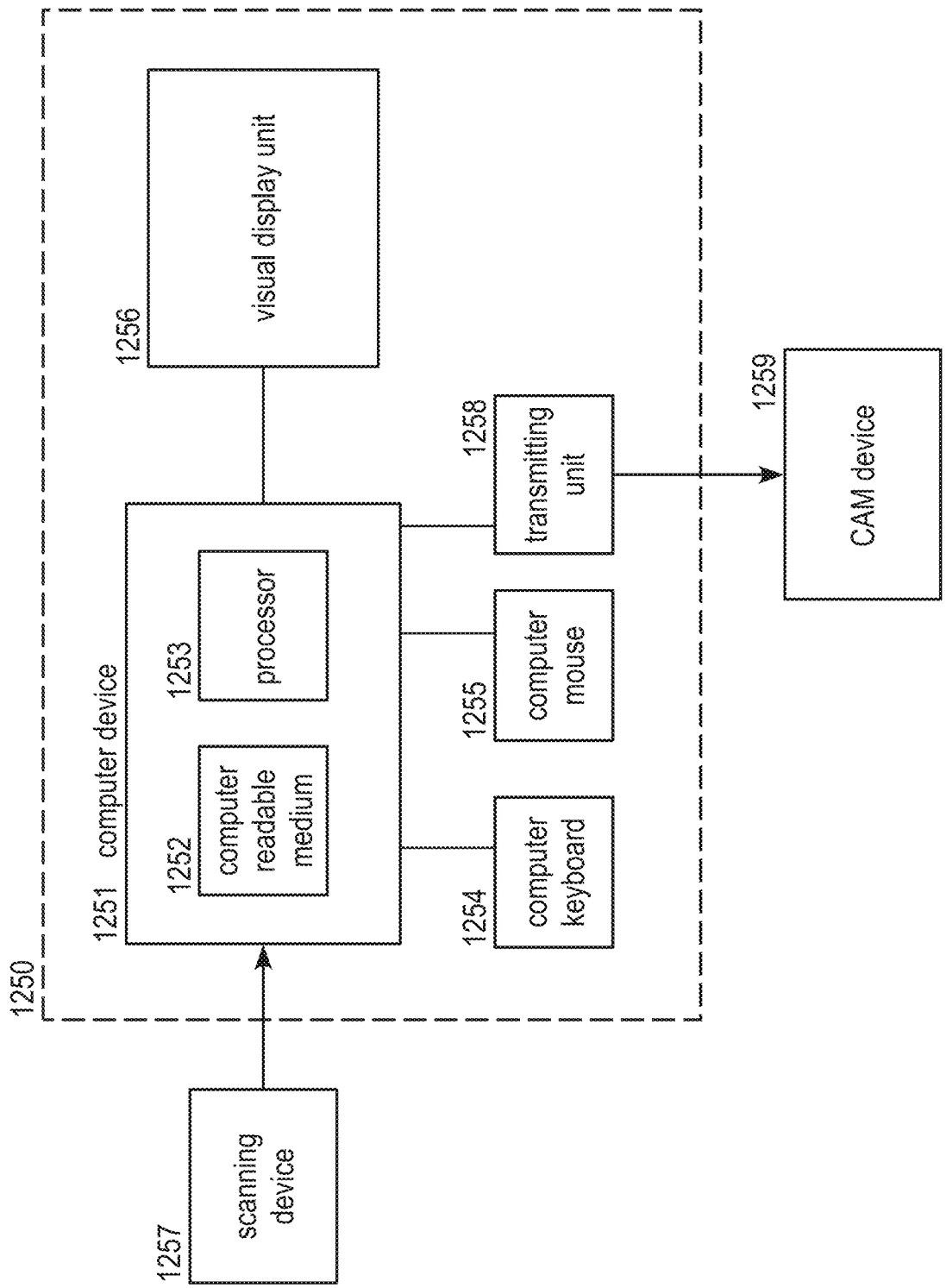
FIG. 12 shows by way of a block diagram, a computerized device for generating a dental preparation guide.

FIG. 12 shows by way of a block diagram a system for generating a dental preparation guide according to an embodiment of the present invention. The system 1250 comprises a computer device 1251 comprising a computer readable medium 1252 and a processor 1253. The system further comprises a visual display unit 1256, a computer keyboard 1254 and a computer mouse 1255 for entering data and activating virtual buttons visualized on the visual display unit 1256. The visual display unit 1256 can e.g. be a computer screen. The computer device 1251 is capable of receiving a digital 3D representation of the patient's set of teeth from a scanning device 1257, such as the TRIOS intra-oral scanner manufactured by 3shape NS, or capable of receiving scan data from such a scanning device and forming a digital 3D representation of the patient's set of teeth based on such scan data. The digital 3D representation may be of a pre-prepared or a prepared set of teeth.

The received or formed digital 3D representation can be stored in the computer readable medium 1252 and provided to the processor 1253. The processor 1253 is configured for virtually removing said at least one tooth from the digital 3D representation of the pre-prepared set of teeth, such that a digital 3D representation of a remaining set of teeth is formed. This can be done based on a 3D sectioning spline defined in relation to the digital 3D representation of the pre-prepared teeth e.g. by the operator using the computer mouse to mark relevant positions on the digital 3D representation of the pre-prepared teeth. A virtual target dental restoration expressing a target shape of the dental restoration can be provided to the processor 1253 from an external source or from the computer readable medium 1252. The processor 1253 is further configured for creating a virtual validation surface for the dental preparation guide based on the virtual target dental restoration, where the validation surface is such that the preparation of the tooth can be validated by the dental preparation guide; and for creating a virtual preparation guide surface by combining the virtual validation surface and at least part of the surface of the digital 3D representation of the remaining set of teeth. While creating the virtual validation surface and/or the virtual preparation guide surface one or more options can be presented to the operator, such as whether to connect the virtual validation surface to the digital 3D representation of the remaining set of teeth using a Boolean addition or by be creating a connecting surface by lofting. The options can be presented in a user interface visualized on the visual display unit 1256.

In some cases, the processor 1253 is further configured for shelling at least a selected part of the virtual preparation guide surface such that the virtual dental preparation guide comprises an inner shell surface and an outer shell surface in the selected part. The system has a unit 1258 for transmitting the shelled virtual preparation guide surface to e.g. a computer aided manufacturing (CAM) device 1259 for manufacturing the dental preparation guide or for manufacturing an intermediate physical model from which the dental preparation guide can be formed by vacuum forming, or to another computer system e.g. located at a milling center where the dental preparation guide or the intermediate physical model is manufactured. The unit for transmitting the virtual 3D model can be a wired or a wireless connection.

The scanning of the patient's set of teeth using the scanning device 1257 is most often performed at dentist's office. The designing and the manufacture of the dental preparation guide can be performed at the dentist's office or at a dental laboratory. In the latter case, the digital 3D representation of the patient's pre-prepared set of teeth can be provided via an internet connection between the dentist and the dental laboratory.

Figure 13:
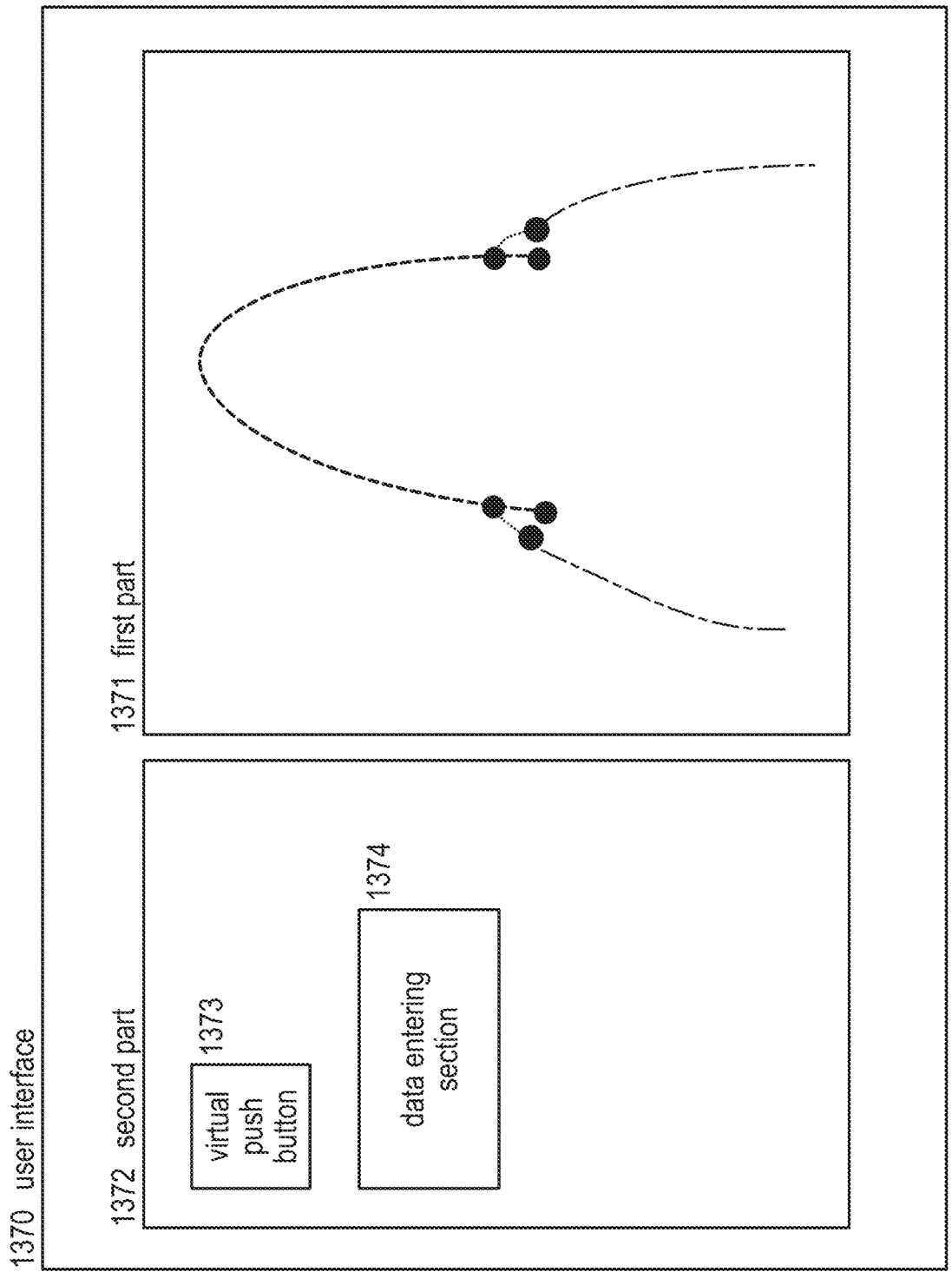
FIG. 13 shows a schematic of a user interface according to an embodiment of the invention.

FIG. 13 shows a schematic of a user interface according to an embodiment of the invention.

The figure shows a first part 1371 of the user interface 1370 in which cross sectional views of different surfaces used in the designing of the dental preparation guide are visualized. In the illustrated example, the virtual validation surface, the digital 3D representation of the remaining set of teeth, the virtual preparation line, the 3D remaining teeth spline, and the 3D validation surface spline of FIG. 4 are seen on the first part.

The second part 1372 of the user interface comprises a data entering section 1374 for entering data relating to e.g. whether the virtual validation surface is to be connected by a Boolean addition or by a surface created by a lofting process. A virtual push button 1373 is configured for providing the virtual preparation guide surface is created by combining the virtual validation surface and at least part of the surface of the digital 3D representation of the remaining set of teeth based on the data entered in the data entering section 1374.

The user interface can be visualized on a visual display unit, such as a computer screen being part of a system configured for implementing the method according to the present invention. The user interface is also configured for performing at least some of the other steps in the method, such as the virtually removing of at least one tooth from the digital 3D representation of the pre-prepared set of teeth when forming the digital 3D representation of a remaining set of teeth. For these steps the virtual push buttons and the data entry sections provided in the second part 1372 may differ from those provided when connecting the virtual surface.

FIG. 15 shows an example dental preparation guide formed as a two-piece device with a first part formed as a temporary crown.

Figure 15A:
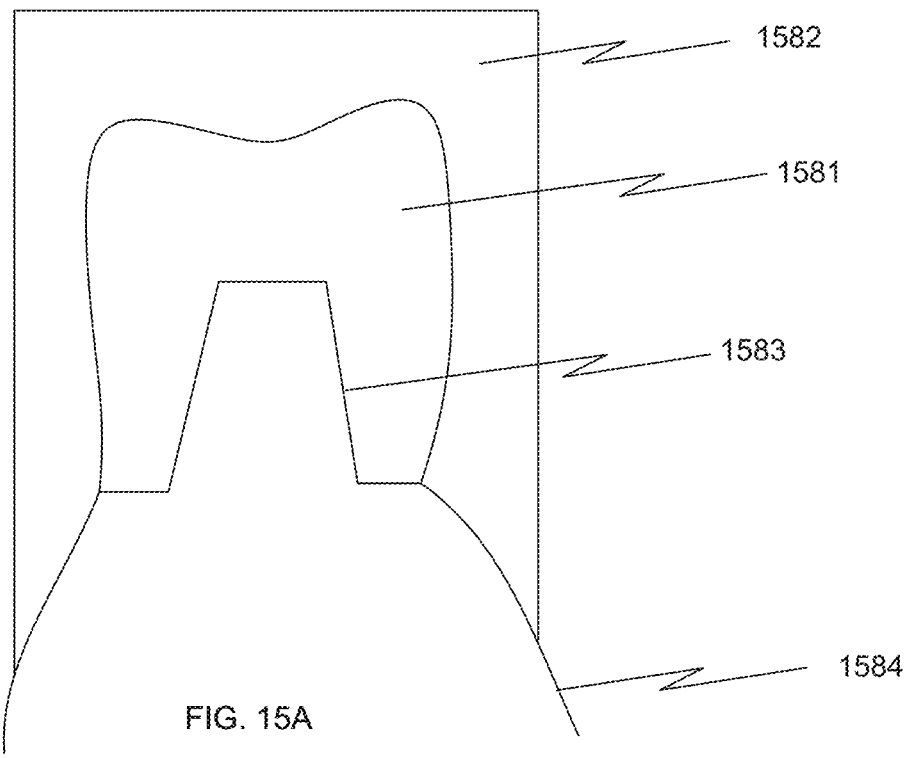
FIGS. 15A through 15C show an example dental preparation guide formed as a two-piece device with a first part formed as a temporary crown.

The two-piece dental preparation guide 1580 illustrated in FIG. 15*a* has a first part 1581 and a second part 1582, where the second part 1582 is designed to have an inner surface configured for engaging the outer surface of the first part 1581 and the second part 1582 can be arranged in relation the first part 1581 such that the first and the second part together form the dental preparation guide 1580. When the two-piece dental preparation guide 1580 is arranged in relation to the patient's set of teeth, the inner surface of the first part 1581 faces the prepared tooth 1583 and the second part contacts the gingiva 1584 at the prepared tooth.

Figure 15B:
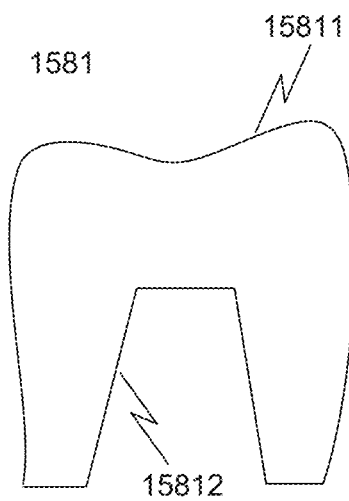

FIG. 15*b* shows the first part 1581 formed as a temporary crown and which is designed to have an outer surface 15812 shaped to resemble a normal tooth surface and an inner surface 15812 with a shape based on the virtual validation surface such that the first part can validate the preparation of the tooth.

Figure 15C:
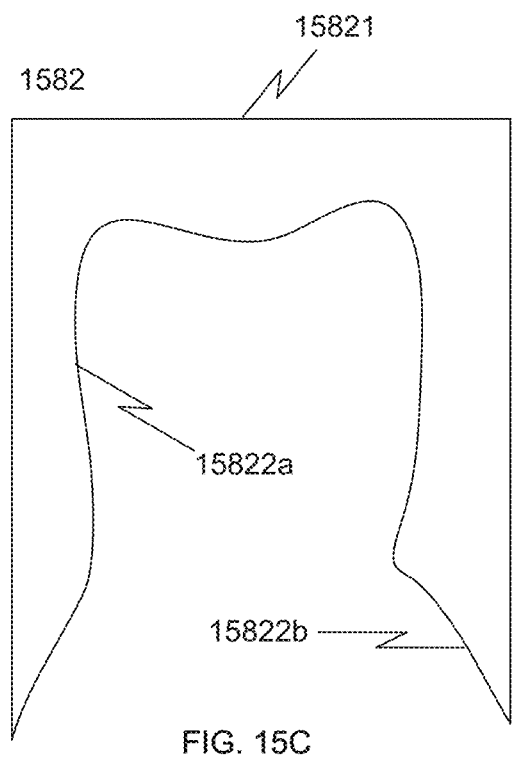

FIG. 15*c* shows the second part 1582 with its inner surface 15822*a*, 15822*b* and outer surface 15821. The inner surface has a portion 15822*a* configured for engaging the outer surface of the first part of the dental preparation guide and a second part 15822*b* configured for contacting the gingiva at the prepared tooth. The first portion 15822*a* provides that the first and second parts of the dental preparation guide can mate and be handled as a coherent unit while the second portion 15822*b* ensures that the dental preparation guide 1580 can be arranged correctly relative to the prepared tooth.

When used for validating the tooth preparation, the two-piece dental preparation guide is operated as one coherent unit the inner surface 15812 of the first part 1581 of the dental restoration is used for the validation. When the dentist as satisfied with the preparation of the tooth the first part 1581 and second part 1582 are disengaged and the first part 1581 can be temporarily secured at the prepared tooth and function as a temporary crown while the final restoration is manufactured based on e.g. a scan of the prepared set of teeth.

Figure 16:
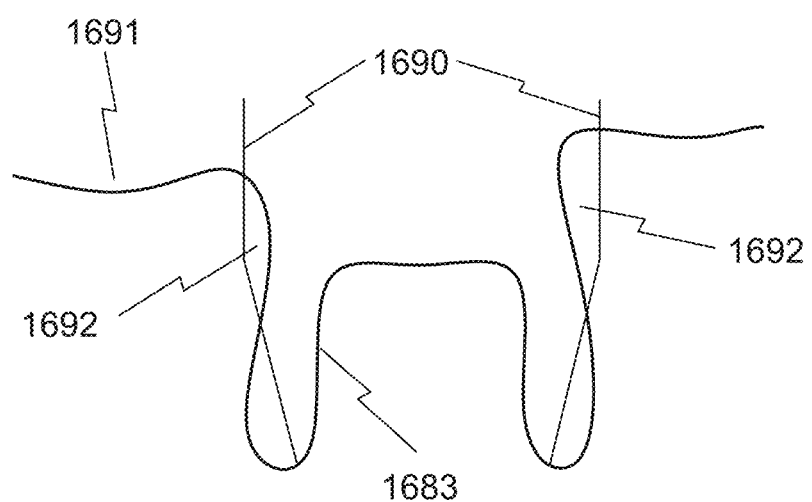
FIG. 16 shows an example of a dental preparation guide generated from a digital 3D representation of the prepared set of teeth and a required minimum thickness of the dental restoration.
Figure 17A:
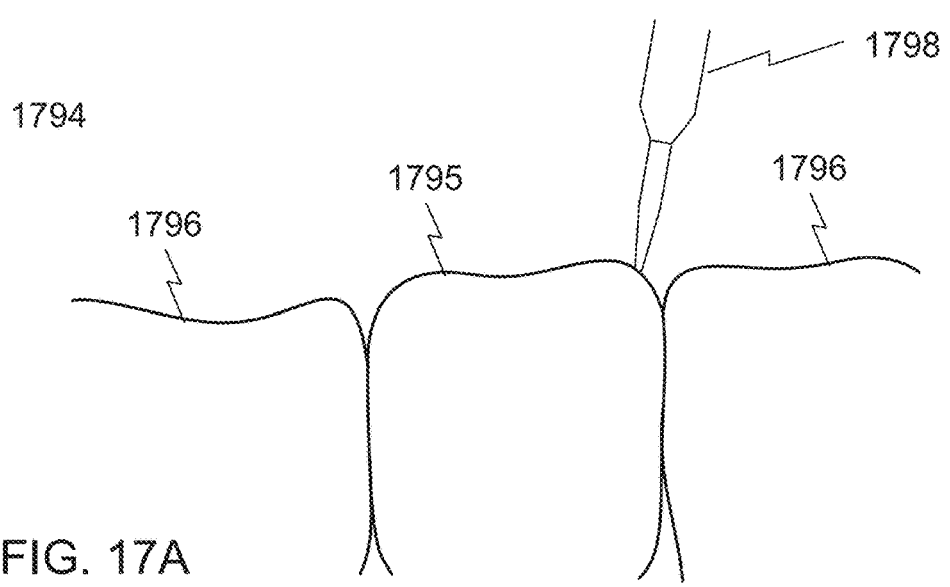
FIGS. 17A through 17C show an example of a preparation of a tooth and a dental preparation guide configured for validating the preparation of the tooth.
Figure 17B:
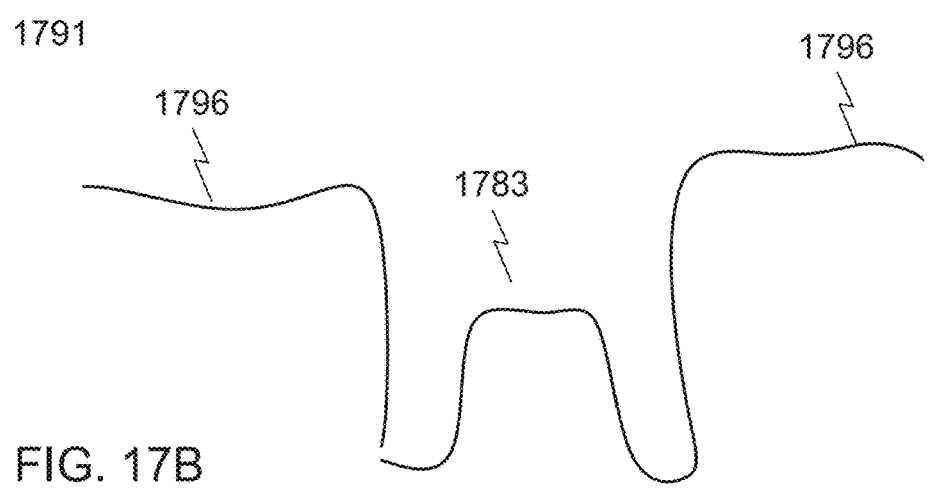
Figure 17C:
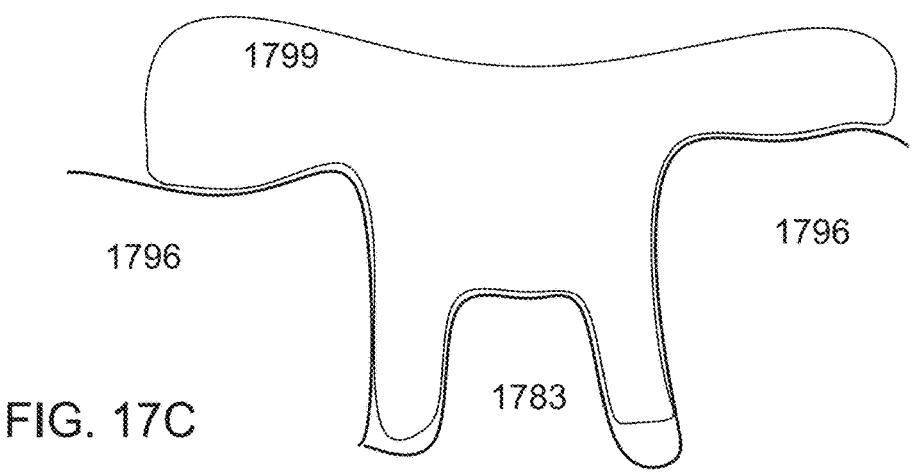

FIG. 16 shows an example of a dental preparation guide generated from a digital 3D representation of the prepared set of teeth and a required minimum thickness of the dental restoration.

The obtained a digital 3D representation of a prepared set of teeth 1691 comprises a portion 1683 corresponding to the prepared tooth. Based on the prepared tooth portion 1683 and a required minimum thickness of the dental restoration a virtual minimum restoration surface 1690 is generated. This surface marks the surface of the smallest dental preparation which can be made to fulfill requirements relating to e.g. the mechanically stable or the color of the dental restoration when arranged at the prepared tooth in its present shape. Any overlaps 1692 between the generated virtual minimum restoration surface 1690 and the obtained digital 3D representation of the prepared set of teeth 1691 can then be determined and the dentist can evaluate whether the overlap is too large or whether a small portion of the neighboring teeth can be grinded away to provide the required space for a dental restoration manufactured according to the virtual minimum restoration surface.

The overlaps 1692 can e.g. be visualized in a user interface by a color coding where e.g. the color red is used to identify the overlapping regions in the digital 3D representation of the prepared set of teeth.

If the dentist decides that further processing is required he removes more tooth material and repeats the process until the overlap is removed or reduced to an insignificant size.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for evaluating a previous preparation of at least one tooth, the method comprising:
   obtaining a digital 3D representation of a prepared set of teeth comprising a digital 3D representation of the previous preparation of at least one tooth;
   generating a virtual 3D dental preparation guide by:
      virtually forming a remaining set of teeth by virtually removing the at least one tooth from the digital 3D representation of the prepared set of teeth; and
      virtually providing a digital 3D representation of a dental restoration expressing a target shape of the dental restoration for the at least one tooth;
   virtually aligning the digital 3D representation of the prepared set of teeth and the virtual 3D dental preparation guide; and
   evaluating the previous preparation of the at least one tooth by determining, based on the virtual alignment, whether further preparation of the previous preparation of the at least one tooth is required to accept a dental restoration.

2. The method according to claim 1, further comprising generating the virtual 3D dental preparation guide or virtual validation surface based on the obtained digital 3D representation of the prepared set of teeth.

3. The method according to claim 1, wherein generating the virtual 3D dental preparation guide further includes:
virtually creating a virtual validation surface based on the digital 3D representation of the dental restoration; and
virtually creating the dental preparation guide by combining the virtual validation surface and at least part of the remaining set of teeth.

4. The method according to claim 1, further comprising visualizing, on a display, the virtually aligned digital 3D representation of the prepared set of teeth and virtual 3D dental preparation guide/virtual validation surface in an overlaid manner; and
evaluating the previous preparation based on the overlaid virtual 3D dental preparation guide/virtual validation surface digital onto 3D representation of the prepared set of teeth.

5. The method according to claim 1, further comprising further preparation of the previous preparation of the at least one tooth when a determination, based on the virtual alignment, is made that the previous preparation of the at least one tooth is required to accept the dental restoration.

6. The method according to claim 1, wherein the evaluation, based on the virtual alignment, comprises changing visualization between visualizing the digital 3D representation of the prepared set of teeth alone and visualizing the digital 3D representation of the prepared set of teeth in combination with a surface of the virtual preparation guide.

7. The method according to claim 1, wherein the evaluation, based on the virtual alignment, comprises toggling on and off the visualization of the virtual dental preparation guide in relation to the digital 3D representation of the prepared teeth to determine part or parts of the previous preparation of the at least one tooth requiring the further preparation.

8. The method according to claim 1, wherein the determination, based on the virtual alignment, comprises determining virtual intersections of or virtual distance between surface of the digital 3D representation of the prepared set of teeth and surface of virtual 3D dental preparation guide/virtual validation surface.

9. The method according to claim 1, further comprising determining a distance between the digital 3D representation of the prepared set of teeth and the virtual validation surface or the virtual dental preparation guide at one or more selected locations on tooth surface.

10. The method according to claim 9, wherein the distance is determined when the virtual validation surface or the virtual dental preparation guide is arranged in a target position in relation to the digital 3D representation of a prepared set of teeth.

11. The method according to claim 9, further comprising visualizing on the display the distance at least at some of said one or more selected locations on the tooth surface, wherein the visualizing the distance on the display includes at least one of visualizing on the display the distances using a distance color coding, indicating the distance using a number, or a difference map.

12. The method according to claim 9, wherein the distance is determined as a minimum value at a specific portion of the validation surface obtained during a virtual movement of the dental preparation guide along an insertion direction into a target position of the dental preparation guide.

13. The method according to claim 1, wherein generating the virtual 3D dental preparation guide includes virtually creating a validation surface based on the target shape of the dental restoration.

14. A non-transitory computer readable medium encoded with a program to cause a computer to execute a method for validating a previous preparation of at least one tooth in a prepared set of teeth for determining whether the prepared tooth is capable of accepting a dental restoration, said method comprising
obtaining a digital 3D representation of a prepared set of teeth comprising a digital 3D representation of the previous preparation of at least one tooth;
generating a virtual 3D dental preparation guide by:
virtually forming a remaining set of teeth by virtually removing the at least one tooth from the digital 3D representation of the prepared set of teeth; and
virtually providing a digital 3D representation of a dental restoration expressing a target shape of the dental restoration for the at least one tooth;
virtually aligning the digital 3D representation of the prepared set of teeth and virtual 3D dental preparation guide; and
evaluating the previous preparation of the at least one tooth by determining, based on the virtual alignment, whether further preparation of the previous preparation of the at least one tooth is required to accept a dental restoration.

15. The non-transitory computer readable medium according to claim 14, wherein generating the virtual 3D dental preparation guide includes:
virtually creating a virtual validation surface based on the digital 3D representation of the dental restoration; and
virtually creating the dental preparation guide by combining the virtual validation surface and at least part of the remaining set of teeth.

16. The non-transitory computer readable medium according to claim 14, wherein the method further comprises changing visualization between visualizing the digital 3D representation of the prepared set of teeth alone and visualizing the digital 3D representation of the prepared set of teeth in combination with a surface of the virtual preparation guide.

17. The non-transitory computer readable medium according to claim 14, wherein the method further comprises toggling on and off the visualization of the virtual dental preparation guide in relation to the digital 3D representation of the prepared teeth to determine part or parts of the previous preparation of the at least one tooth requiring the further preparation.

18. The non-transitory computer readable medium according to claim 14, wherein the method further comprises determining virtual intersections of or virtual distance between surface of the digital 3D representation of the prepared set of teeth and surface of virtual 3D dental preparation guide/virtual validation surface.

19. The non-transitory computer readable medium according to claim 14, wherein the method further comprises determining a distance between the digital 3D representation of the prepared set of teeth and the virtual validation surface or the virtual dental preparation guide at one or more selected locations on tooth surface.

20. The non-transitory computer readable medium according to claim 14, wherein the method further comprises visualizing on a display the distance at least at some of said one or more selected locations on the tooth surface, wherein the visualizing the distance on the display includes at least one of visualizing on the display the distances using a distance color coding, indicating the distance using a number, or a difference map.

21. The non-transitory computer readable medium according to claim 14, wherein the method further comprises determining a minimum distance value at a specific portion of the validation surface obtained during a virtual movement of the dental preparation guide along an insertion direction into a target position of the dental preparation guide.

22. The non-transitory computer readable medium according to claim 14, wherein generating the virtual 3D dental preparation guide includes virtually creating a validation surface based on the target shape of the dental restoration.

* * * * *